United States Patent [19]

Mookherjee et al.

[11] Patent Number: 4,595,525
[45] Date of Patent: Jun. 17, 1986

[54] COMPOSITION AND PROCESS FOR AUGMENTING, ENHANCING OR IMPARTING A LEATHER AROMA TO CONSUMABLE MATERIALS

[75] Inventors: Braja D. Mookherjee, Holmdel; Robert W. Trenkle, Bricktown, both of N.J.

[73] Assignee: International Flavors & Fragrances Inc., New York, N.Y.

[21] Appl. No.: 656,359

[22] Filed: Oct. 1, 1984

[51] Int. Cl.$^4$ .................................................. A61K 7/46
[52] U.S. Cl. ........................... 252/522 R; 252/174.11; 252/8.6; 424/70; 424/69
[58] Field of Search .................. 252/522 R, 86, 174.11; 424/69, 70

[56] References Cited

U.S. PATENT DOCUMENTS 4,434,086  2/1984  Hill et al. ......................... 252/522 R

OTHER PUBLICATIONS

Swamer et al., J.A.C.S., vol. 72, pp. 1352–1356.
Fuehrer, Chem. Abst., vol. 79, #9763q (1973).

Primary Examiner—James H. Reamer
Attorney, Agent, or Firm—Arthur L. Liberman

[57] ABSTRACT

Described is the process for augmenting, enhancing or imparting leather aromas to consumable materials including perfume compositions, colognes, perfumed polymers and perfumed articles including solid or liquid anionic, cationic, nonionic or zwitterionic detergents, fabric softener compositions, fabric softener articles, hair preparations, cosmetic powders and the like, by adding thereto a composition of matter consisting of the following ingredients:

"A": At least one substance having the structure:

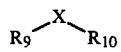

in an amount of from about 1% up to about 5% wherein $R_9$ represents $C_9$–$C_{11}$ straight-chain alkyl and wherein $R_{10}$ represents methyl and X is a moiety selected from the group consisting of:

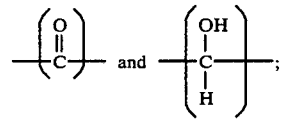

"B": At least one compound having the structure:

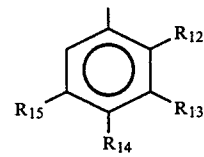

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

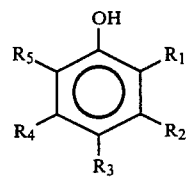

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

(Abstract continued on next page.)

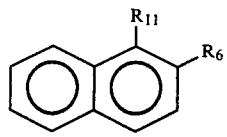

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

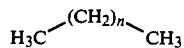

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

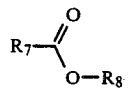

in an amount of from about 20% up to about 60% wherein n represents an integer of from 8 up to 28;

"G": Optionally, the compound having the structure:

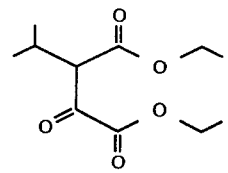

in an amount of from 0 up to about 6%; and

"H": Optionally, the compound having the structure:

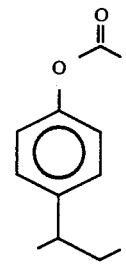

in an amount of from 0 up to about 6% with the requirement that:

$$\Sigma[A + B + C + D + E + F + G + H]$$

equal 100%.

9 Claims, 14 Drawing Figures

GLC PROFILE FOR FRACTION I OF EXAMPLE I.

GLC PROFILE FOR FRACTION 2 OF EXAMPLE I.

GLC PROFILE FOR FRACTION 3 OF EXAMPLE I.

GLC PROFILE FOR FRACTION 4 OF EXAMPLE I.

GLC PROFILE FOR DISTILLATION FRACTIONS 4-10 OF EXAMPLE II.

GLC PROFILE FOR DISTILLATION FRACTIONS 19-25 OF EXAMPLE II.

GLC PROFILE FOR EXAMPLE II . PHENOLIC SECTION .

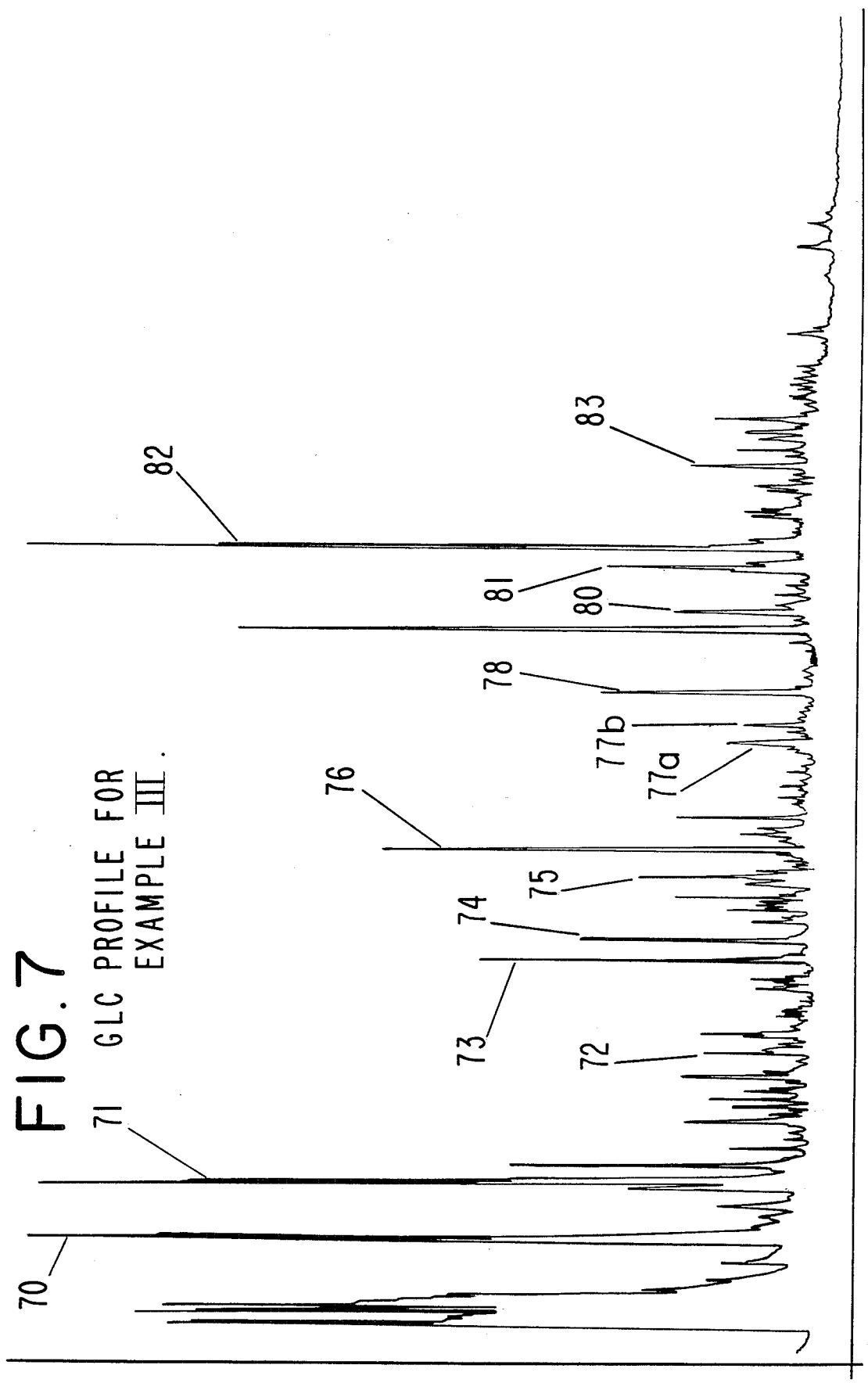
FIG. 7 GLC PROFILE FOR EXAMPLE III.

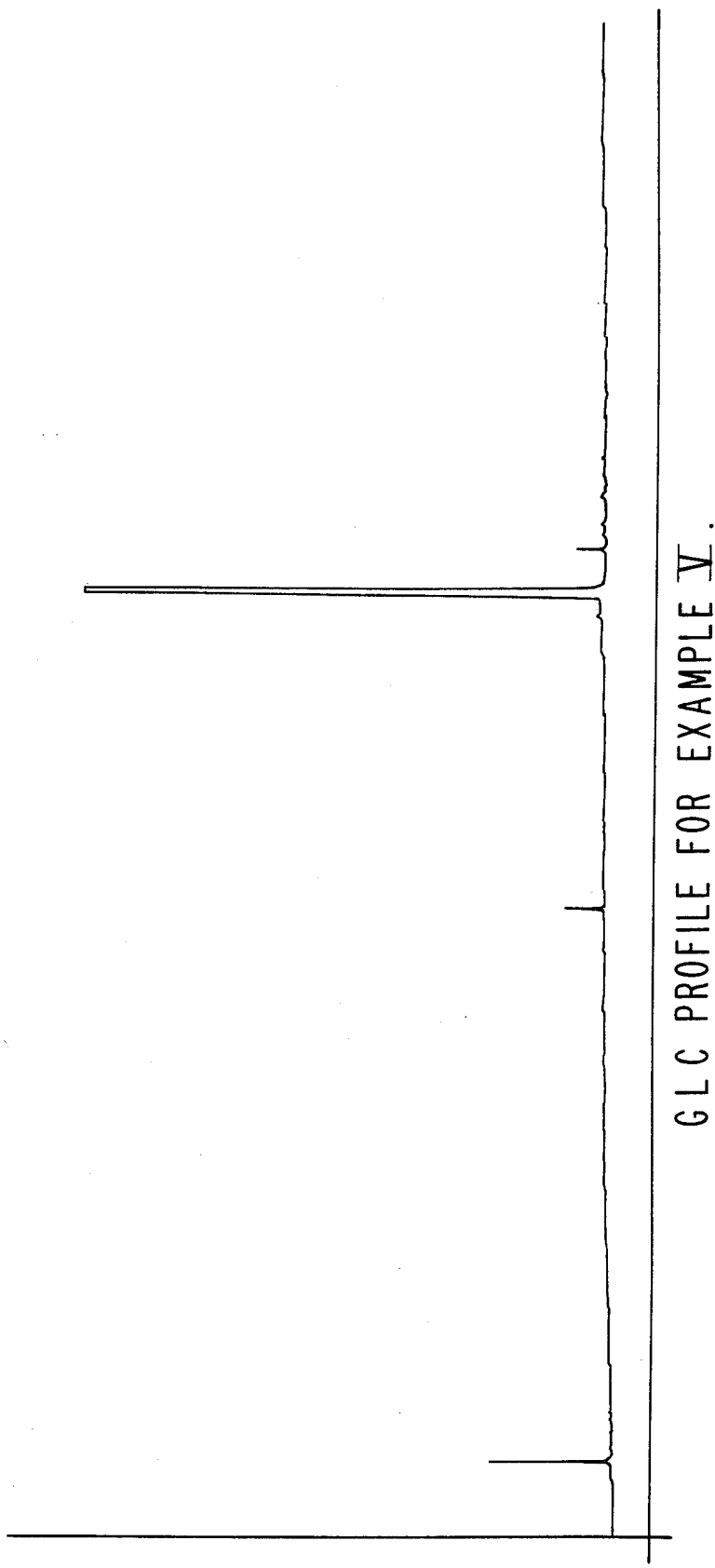

NMR SPECTRUM FOR EXAMPLE V.

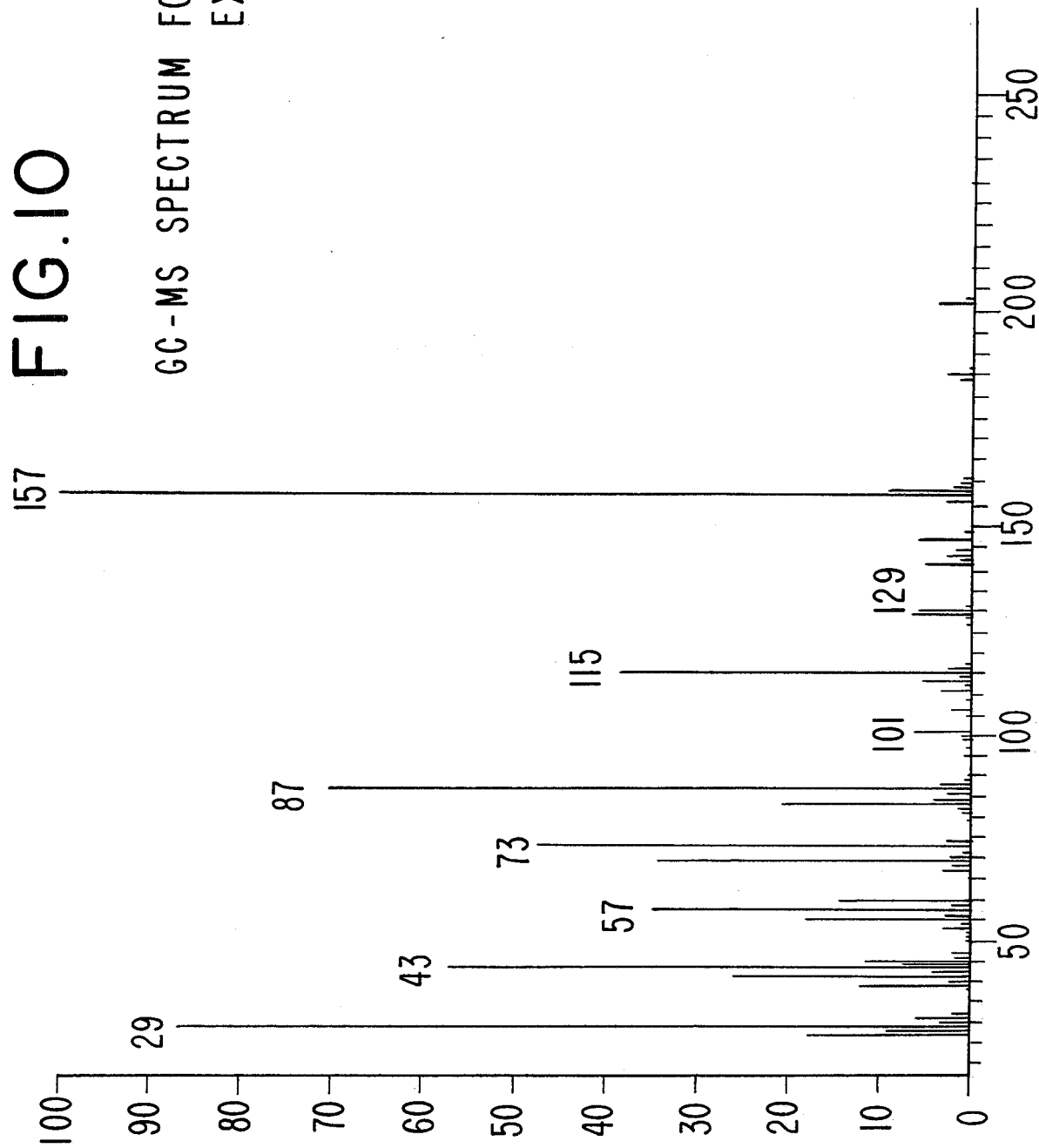
FIG. 10 GC-MS SPECTRUM FOR EXAMPLE V.

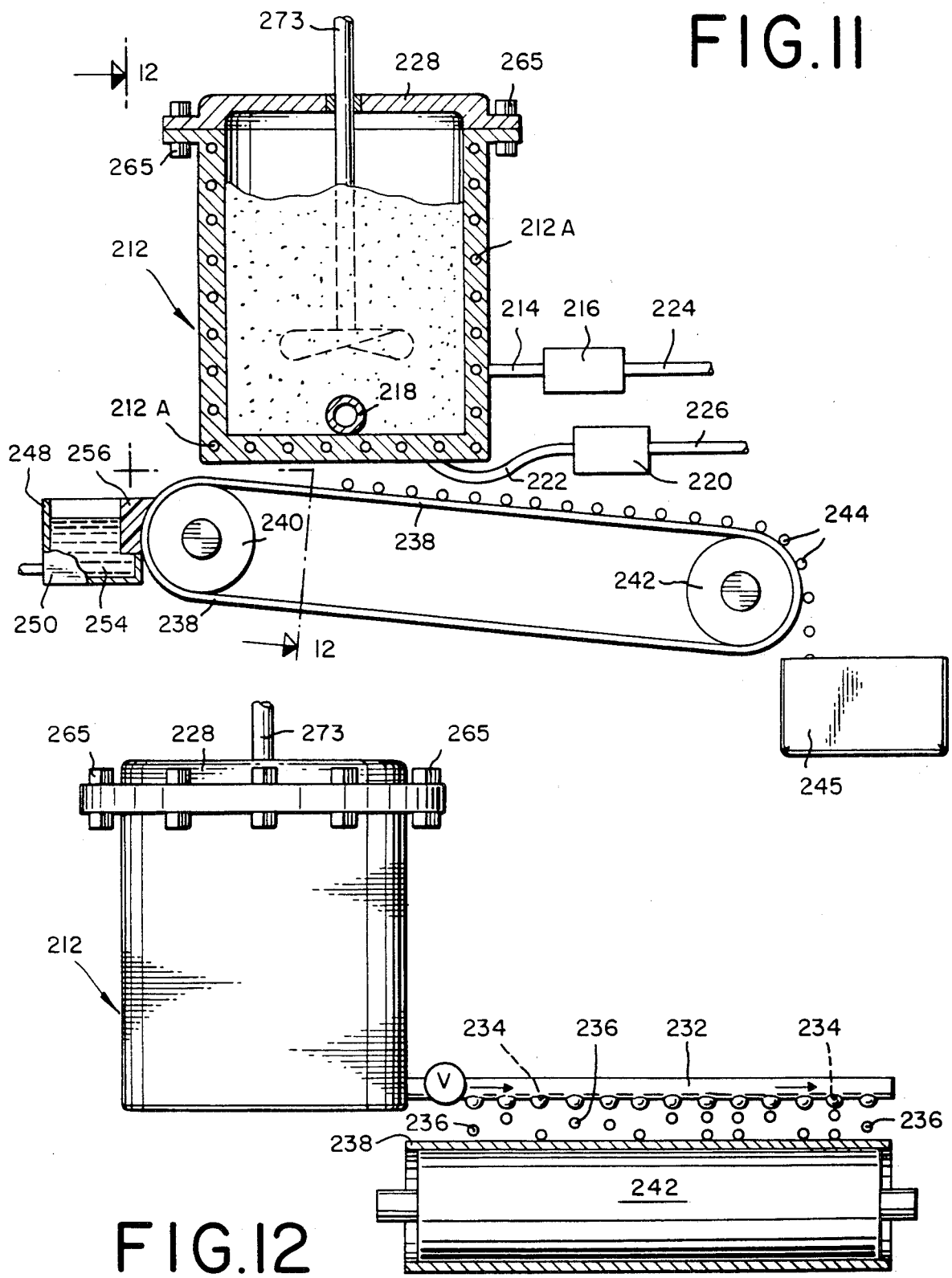

COMPOSITION AND PROCESS FOR AUGMENTING, ENHANCING OR IMPARTING A LEATHER AROMA TO CONSUMABLE MATERIALS

BACKGROUND OF THE INVENTION

The instant invention relates to the use of a mixture of conpounds of specific ranges of proportions in augmenting, enhancing or imparting leather aromas to consumable materials or in consumable materials.

In the perfumery art, there is considerable need for substituents having natural leathery type aroma nuances.

A limited number of materials which give rise to such a property are available from natural sources, e.g., leather extraction as indicated by Arctander (I) "Perfume and Flavor Materials of Natural Origin", (1960) at column 350.

Furthermore, Arctander (II) "Perfume and Flavor Chemicals (Aroma Chemicals), Volume I (1969) at monograph 1328, discloses ortho-ethyl phenol having the structure:

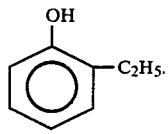

Arctander (II) further indicates that this ortho-ethyl phenol "could find some use in the temporarily modern "leather"-like fragrance types . . . and in various basis requiring . . . leather-like notes. The material carriers with it the usual disadvantages of a phenol: Tendency to discolor in daylight and sensitivity to iron, alkali and air . . . ". At monograph 573, Arctander discloses carvacrol (2-methyl-5-isopropyl phenol) having the structure:

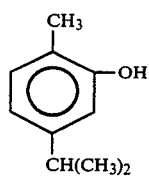

as having use in perfumes for its herbaceous odor and spicy undertone. Arctander states, with regard to carvacrol:

"Used in perfume compositions mainly in industrial fragrances, certain types of heavy-duty household fragrances, soap perfumes, etc. It has good power, and is fairly stable in ordinary soaps, in spite of its hydroxyl-group (phenol radicle)."

Nothing in the prior art, however, shows the unexpected, unobvious and advantageous properties of the mixture:

"A": At least one substance having the structure:

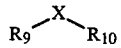

in an amount of from about 1% up to about 5% wherein $R_9$ represents $C_9$–$C_{11}$ straight-chain alkyl and wherein $R_{10}$ represents methyl and X is a moiety selected from the group consisting of:

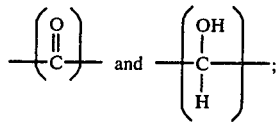

"B": At least one compound having the structure:

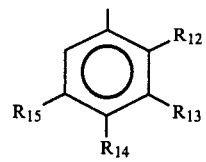

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

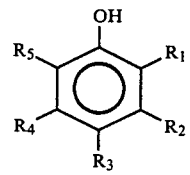

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

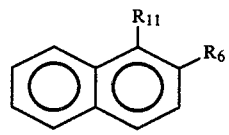

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

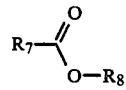

in an amount of from about 30% up to about 70% wherein $R_7$ represents $C_{11}$, $C_{13}$, or $C_{15}$ straight-chain alkyl and $R_8$ represents $C_1$–$C_3$ lower alkyl;

"F": At least one compound having the structure:

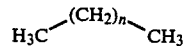

in an amount of from about 20% up to about 60% wherein n represents an integer of from 8 up to 28;

"G": Optionally, the compound having the structure:

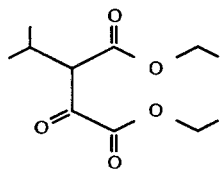

in an amont of from 0 up to about 6%; and

"H": Optionally, the compound having the structure:

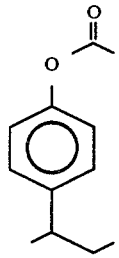

in an amount of from 0 up to about 6% with the requirement that;

Σ[A + B + C + D + E + F + G + H]

equal 100% in augmenting, enhancing or imparting natural leathery aromas to consumable materials.

BRIEF DESCRIPTION OF THE DRAWINGS

FIG. 7 is the GLC profile for the leather head space collected according to Example III (Conditions: 400' OV-1 column programmed over 60°-190° C. per minute).

FIG. 8 is the GLC profile for the reaction product of Example V containing the compound having the structure:

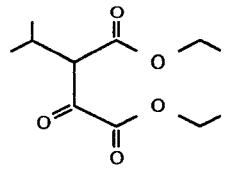

(Conditions: 50M×0.32M carbowax 20M fused silica capillary column programmed at 50°-225° C. at 2° C. per minute).

Figure 9:
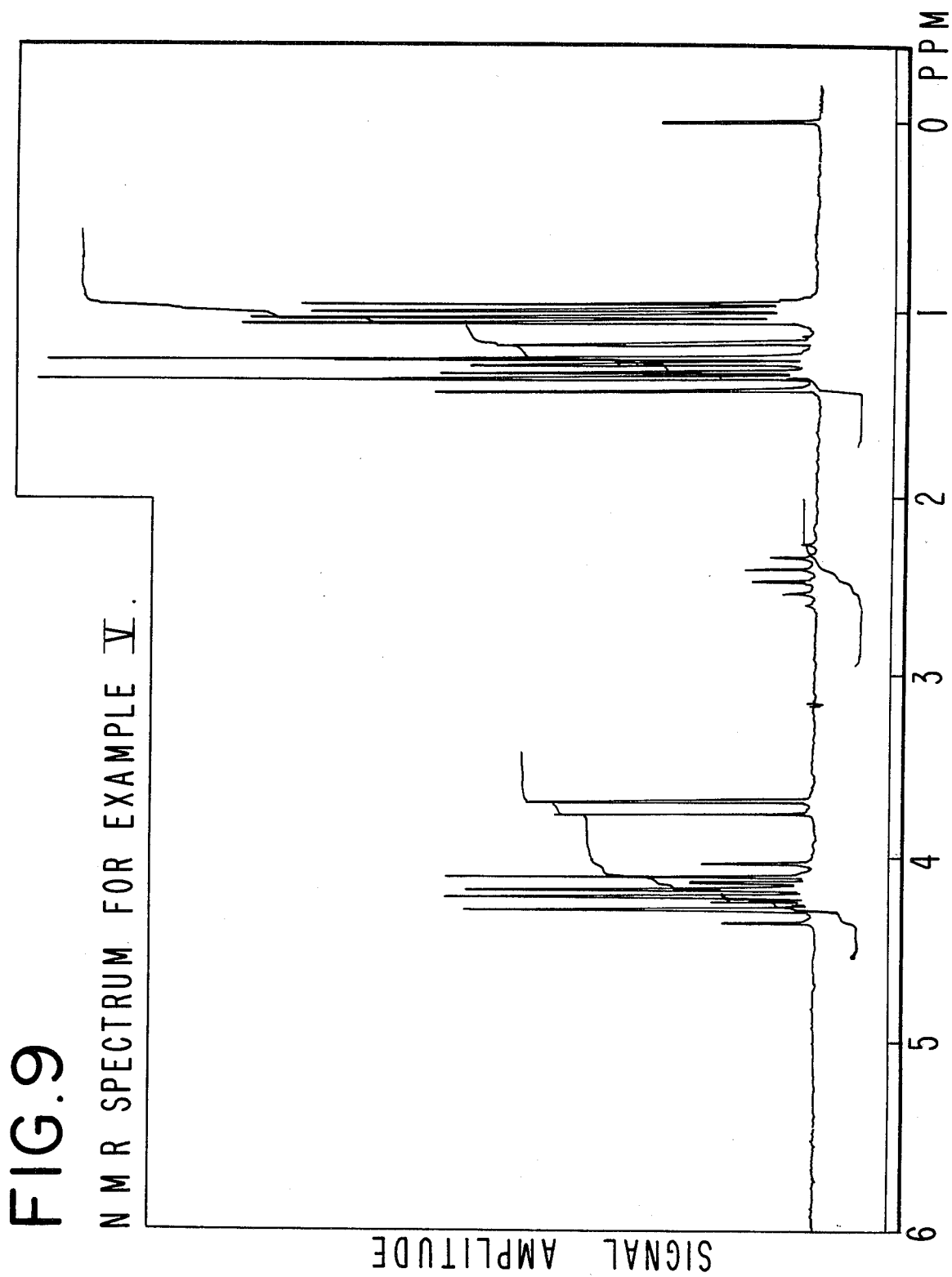

FIG. 9 is the NMR spectrum for the compound having the structure:

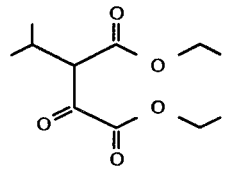

prepared according to Example V (Conditions: Field strength: 100 MHz; solvent: CFCl₃).

FIG. 10 is the GC-MS spectrum for the compound having the structure:

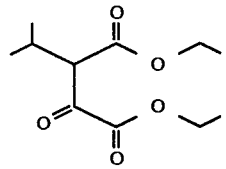

prepared according to Example V.

FIG. 11 is a partial slide elevation and partial sectional view of an apparatus for forming leather-scented polymers using at least one of the mixtures defined according to the formulation:

"A": At least one substance having the structure:

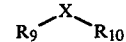

in an amount of from about 1% up to about 5% wherein R₉ represents C₉-C₁₁ straight-chain alkyl and wherein R₁₀ represents methyl and X is a moiety selected from the group consisting of:

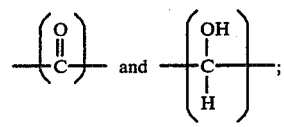

"B": At least one compound having the structure:

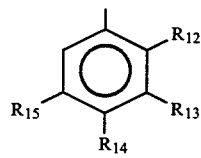

in an amount of from about 3 up to about 7% wherein each of $R_{12}$-$R_{15}$ represents hydrogen or $C_1$-$C_4$ alkyl with the proviso that at least two of $R_{12}$-$R_{15}$ represents hydrogen;

"C": At least one compound having the structure:

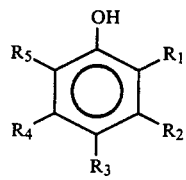

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl; "D": Optionally, at least one compound having the structure:

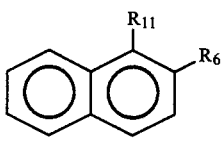

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

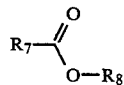

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

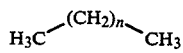

in an amount of from about 20% up to about 60% wherein n represents an integer of from 8 up to 28;

"G": Optionally, the compound having the structure:

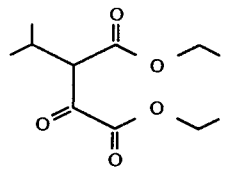

in an amount of from 0 up to about 6%; and

"H": Optionally, the compound having the structure:

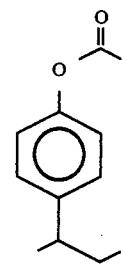

in an amount of from 0 up to about 6% with the requirement that:

$$\Sigma[A + B + C + D + E + F + G + H]$$

equal 100%.

FIG. 12 is a section taken on line 12—12 of FIG. 11.

DETAILED DESCRIPTION OF THE DRAWINGS

Figure 1:
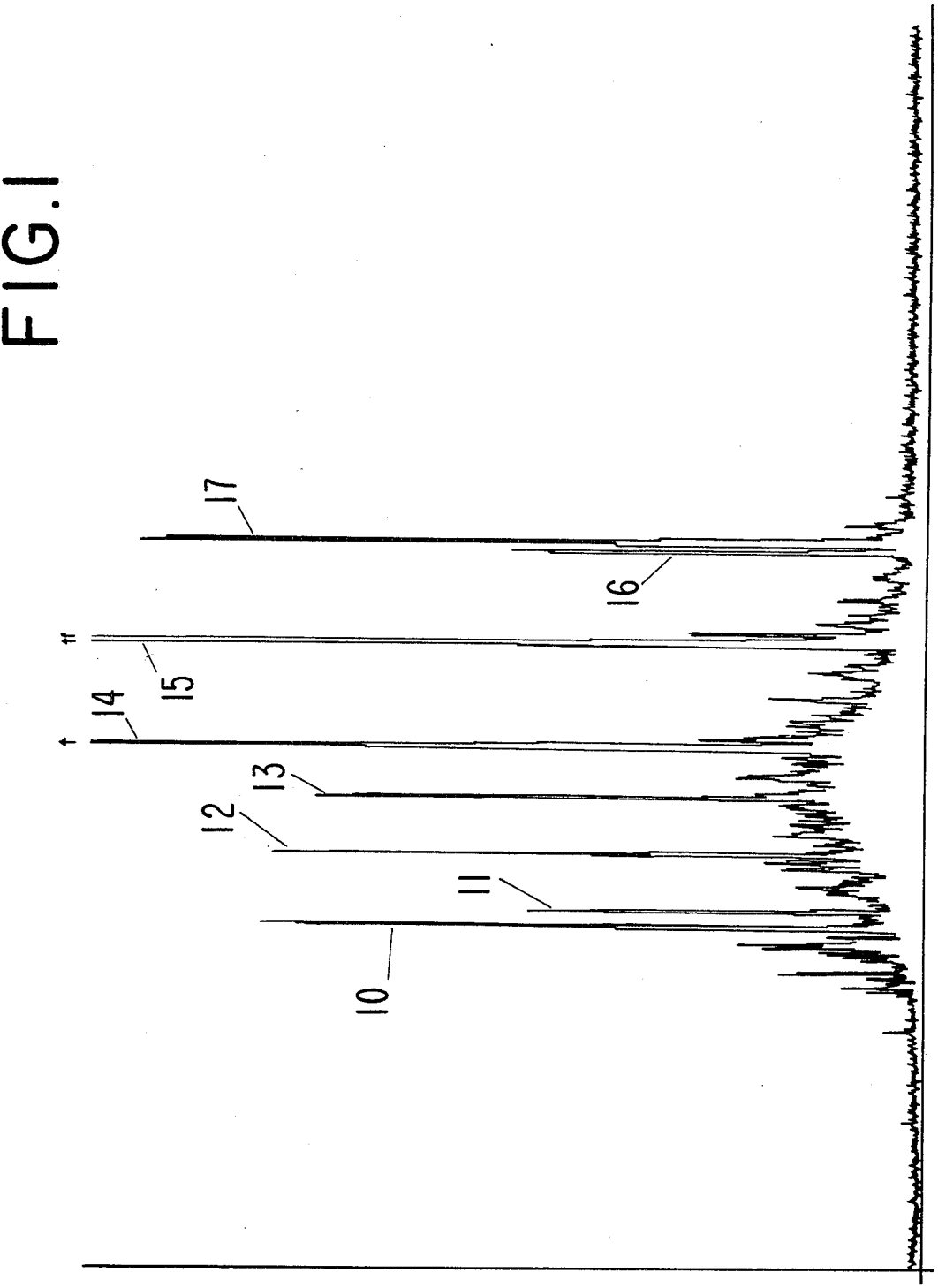
FIG. 1 is the GLC profile for the crude extract of vegetable tanned leather prior to distillation prepared according to Example I (Conditions: Se-30, 50M×0.032" glass capillary column programmed at 80°-220 ° C. at 2° C. per minute).

FIG. 1 is the GLC profile for the crude extract of vegetable tanned leather (before distillation) (Conditions: 50M×0.032"Se-30 glass capillary column programmed at 80°-220° C. at 2° C. per minute). The peak indicated by reference numeral 10 is the peak for n-octadecane. The peak indicated by reference numeral 11 is the peak for n-heptadecane. The peak indicated by reference numeral 12 is the peak for n-nonadecane. The peak indicated by reference numeral 13 is the peak for n-eicosane, a 20 carbon straight chain hydrocarbon. The peak indicated by reference numeral 14 is the peak for methyl myristate. The peak indicated by reference numeral 15 is the peak for methyl polmatate. The peak indicated by reference numeral 16 is the peak for methyl stearate. The peak indicated by reference numeral 17 is the peak for methyl octadecenoate.

Figure 6A:
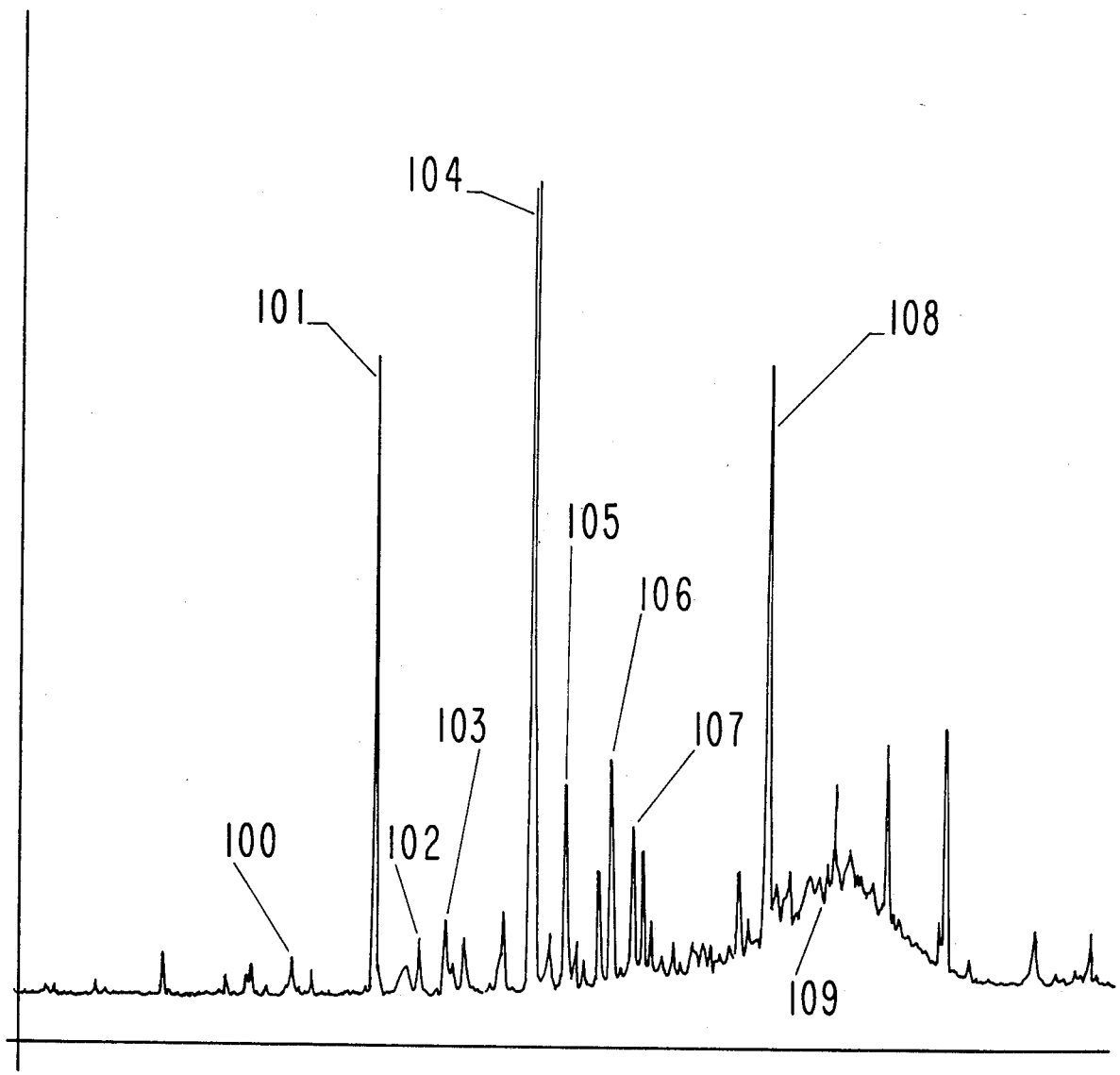
FIG. 6A is the GLC profile for bulked distillation fractions 4-10 of the extract of Example II (Conditions: carbowax fused silica column programmed at 60°-220° C. at 2° C. per minute).

FIG. 6A is the GLC profile for bulked distillation fractions 4-10 of the crude extract of Example II (Conditions: carbowax fused silica column programmed at 60°-220° C. at 2° C. per minute). The peak indicated by reference numeral 100 is the peak for 2,6-di-t-butyl-4-methyl phenol. The peak indicated by reference numeral 101 is the peak for 2-methyl phenol. The peak indicated by reference numeral 102 is the peak for 2,3,6-trimethyl phenol. The peak indicated by reference nunmeral 103 is the peak for 2,4,6-trimethyl phenol. The peak indicated by reference numeral 104 is the peak for 2-n-propyl phenol. The peak indicated by reference numeral 105 is the peak for 4-ethyl phenol. The peak indicated by reference numeral 106 is the peak for 2,3,5-trimethyl phenol. The peak indicated by reference numeral 107 is the peak for 2-t-butyl-4-methyl phenol. The peak indicated by reference numeral 108 is the peak for 3,5-diisopropyl phenol. The peak indicated by reference numeral 109 is the peak for 2-chloro phenol combined with 4-chloro phenol.

Figure 6B:
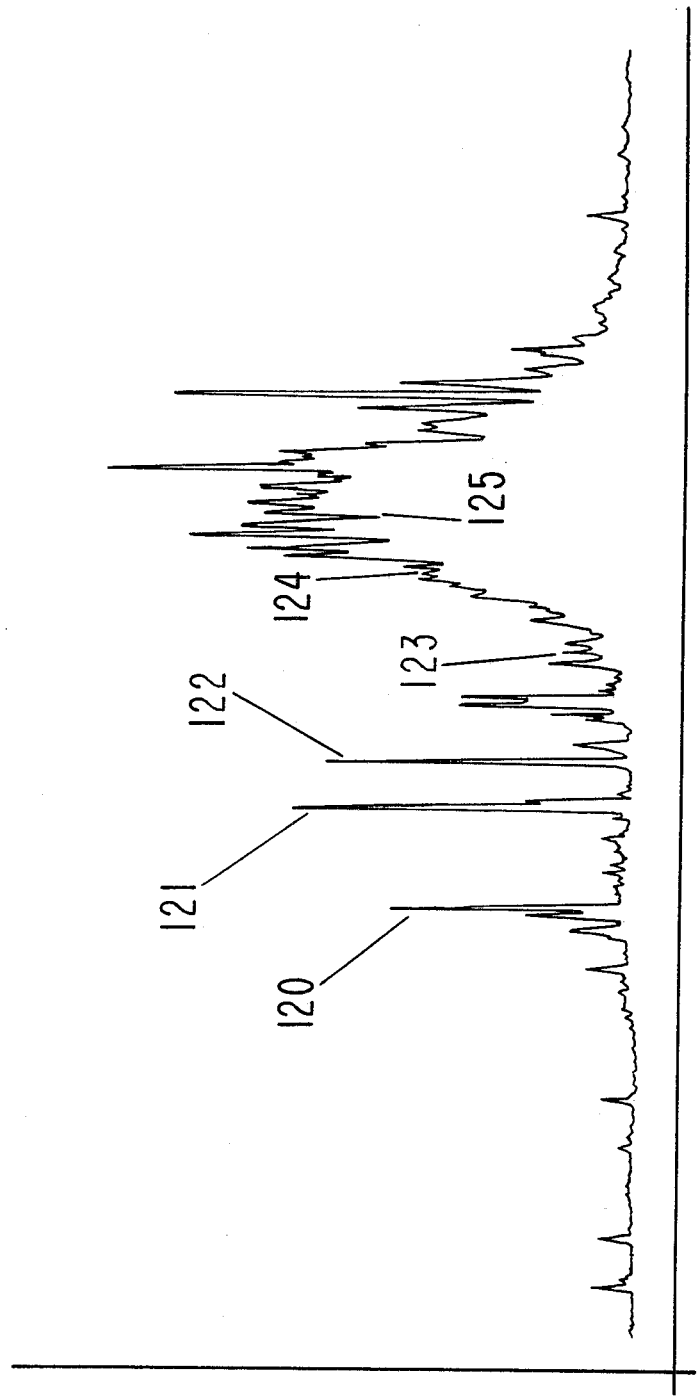
FIG. 6B is the GLC profile for distillation fractions 19-25 of the distillation product of the extract of Example II (Conditions: carbowax fused silica column programmed at 60°-220° C. at 2° C. per minute).

FIG. 6B is the GLC profile for bulked distillation fractions 19–25 of the distillation of the extraction product of Example II (Conditions: Carbowax fused silica column programmed at 60°–220° C. at 2° C. per minute). The peak indicated by reference numeral 120 is the peak for 3-methyl phenol.

The peak indicated by reference numeral 121 is the peak for 4-ethyl-phenol. The peak indicated by reference numeral 122 is the peak for 2-methyl-5-isopropyl phenol. The peak indicated by reference numeral 123 is the peak for 4-n-butyl phenol. The peak indicated by reference numeral 124 is the peak for 3,5-diisopropyl phenol. The peak indicated by reference numeral 125 is the peak for the mixture of 3-chloro phenol and 4-cholor phenol.

Figure 6C:
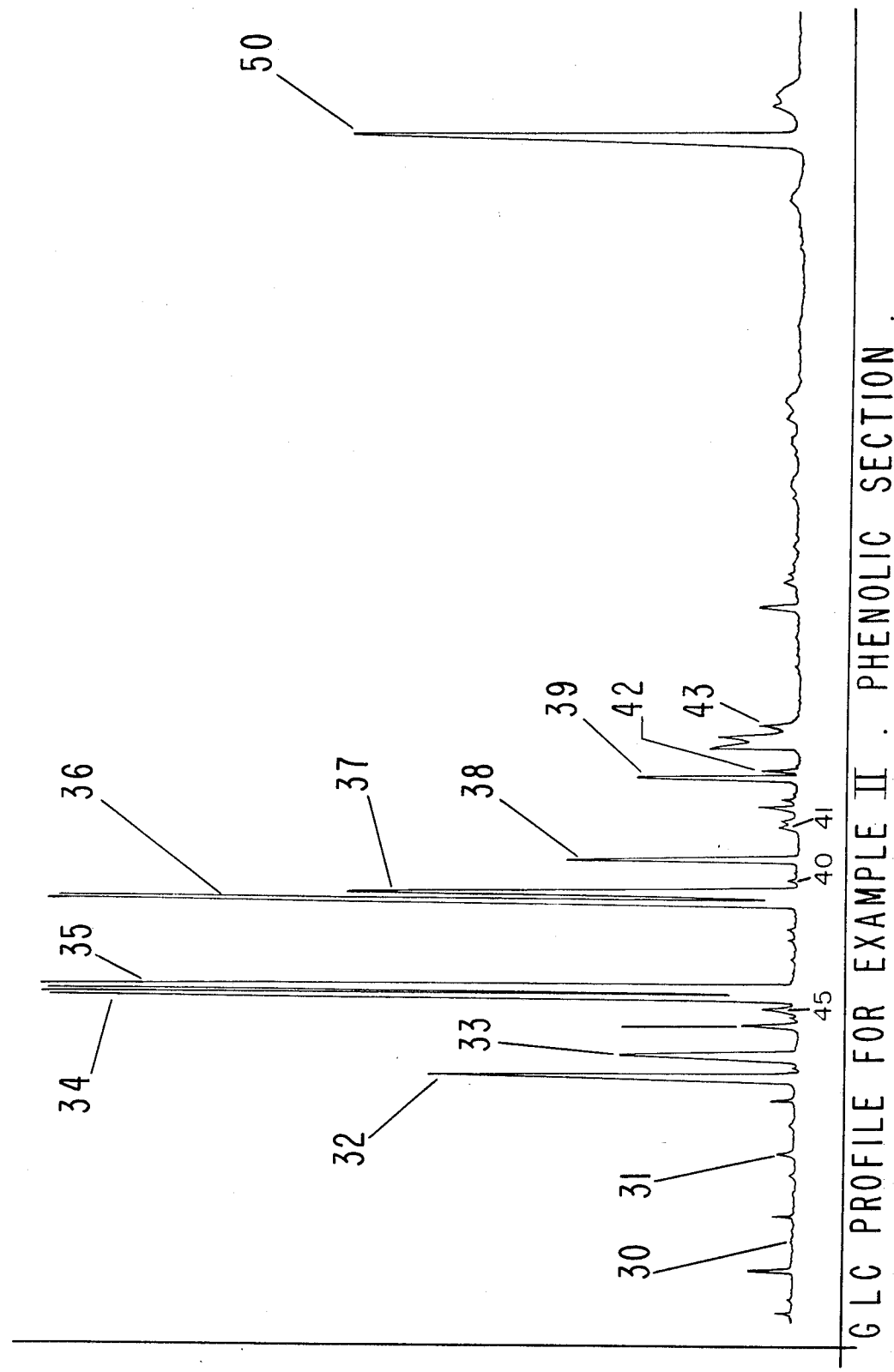
FIG. 6C is the GLC profile for the phenolic section of the extract of Example II (Conditions: Carbowax fused silica column programmed at 60°-220° C. per minute).

FIG. 6C is the GLC profile for the "phenolic" section of the extraction product of Example II (Conditions: Carbowax fused silica column programmed at 60°–220° C. at 2° C. per minute).

The peak indicated by reference numeral 30 is the peak for 2-methyl phenol.

The peak indicated by reference numeral 31 is the peak for 2,6-di-t-butyl-4-methyl phenol. The peak indicated by reference numeral 32 is the peak for the mixture of 2-methyl phenol and 2,4,6-trimethyl phenol. The peak indicated by reference numeral 33 is the peak for 2,6-di-t-butyl phenol. The peak indicated by reference numeral 34 is the peak for 4-methyl phenol. The peak indicated by reference numeral 35 is the peak for 3-methyl phenol. The peak indicated by reference numeral 36 is the peak for 4-ethyl phenol and/or 3,5-dimethyl phenol. The peak indicated by reference numeral 37 is the peak for 3-ethyl phenol. The peak indicated by reference numeral 38 is the peak for 3,5-dimethyl phenol and/or 3,4-dimethyl phenol. The peak indicated by reference numeral 39 is the peak for 4-(2′-butyl) phenol. The peak indicated by reference numeral 40 is the peak for 2-isopropyl-5-methyl phenol. The peak indicated by reference 41 is the peak for 3-methyl-4-t-butyl phenol. The peak indicated by reference numeral 42 is the peak for 4- isopropyl phenol. The peak indicated by reference numeral 43 is the peak for 3,5-diisopropyl phenol. The peak indicated by reference numeral 44 is the peak for 2,3,6-trimethyl phenol. The peak indicated by reference numeral 45 is the peak for 2-ethyl phenol. The peak indicated by reference numeral 50 is the peak for β-naphthol.

FIG. 7 is the GLC profile for the purged leather head space produced according to Example III (Conditions: 400′ OV-1 column programmed at 60°–190° C. at 2° C. per minute).

The peak indicated by reference numeral 70 is the peak for toluene. The peak indicated by reference numeral 71 is the peak for 1,2-dimethyl benzene. The peak indicated by reference numeral 72 is the peak for n-decane. The peak indicated by reference numeral 73 is the peal for diethyl benzenes. The peak indicated by reference numeral 74 is the peak for diethyl bezenes. The peak indicated by reference numeral 75 is the peak for naphthalene. The peak indicated by reference numeral 76 is the peak for the silicone. The peak indicated by reference numerals 77A and 77B are the peaks for methyl naphthalenes. The peak indicated by reference numeral 78 is the peak for n-tridecane. The peak indicated by reference numeral 79 is the peak for diphenyl and/or acenaphthene. The peal indicated by reference numeral 80 is the peak for diphenyl oxide. The peak indicated by reference numeral 81 is the peak for n-tetradecane. The peak indicated by reference numeral 82 is the peak for thujopsene (an apparent contamination). The peak indicated by reference numeral 83 is the peak for 2,6di-t-butyl-4-methyl phenol.

Referring to the drawings in FIGS. 11 and 12, the invention embodied therein comprises a device for forming leather-scented polymer pellets (e.g., polyethylene, polypropylene or mixtures of polyepsilon, caprolactone and polyethylene or polypropylene or copolymers of polyvinyl acetate and polyethylene or the like) which comprises a vat or container 210 into which a mixture of polymers such as polyethylene and a mixture defined thusly:

"A": At least one substance having the structure:

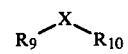

in an amount of from about 1% up to about 5% wherein $R_9$ represents $C_9$–$C_{11}$ straight-chain alkyl and wherein $R_{10}$ represents methyl and X is a moiety selected from the group consisting of:

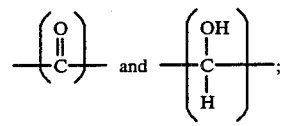

"B": At least one compound having the structure:

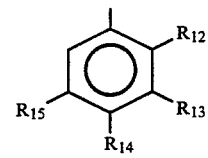

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

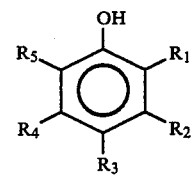

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

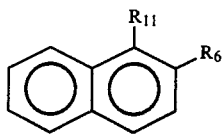

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

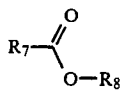

in an amount of from about 30% up to about 70% wherein $R_7$ represents $C_{11}$, $C_{13}$, or $C_{15}$ straight-chain alkyl and $R_8$ represents $C_1$–$C_3$ lower alkyl;

"F": At least one compound having the structure:

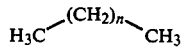

in an amount of from about 20% up to about 60% wherein n represents an integer of form 8 up to 28;

"G": Optionally, the compound having the structure:

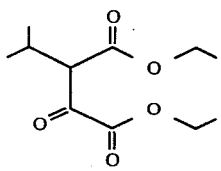

in an amount of from 0 up to about 6%; and

"H": Optionally, the compound having the structure:

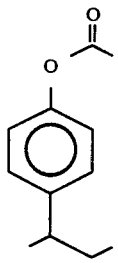

in an amount of from 0 up to about 6% with the requirement that:

$$\Sigma[A + B + C + D + E + F + G + H]$$

The container is closed by an air-tight lid 228 claimped to the container by claimps 265. A stirrer 273 traverses the lid or cover 228 in air-tight manner and is rotated in a suitable manner. The surrounding cylinder 212 having heating coils which are supplied with electrical current through cable 214 from a rheostat or control 216 is operated to maintain the temperature inside the container 210 such that the polymer such as polyethylene in the container will be maintained at a molten or liquid state. It has been found advantageous to employ a colorless, odorless polymer such as low density polyethylene with a viscosity ranging between 180 and 220 centistokes and having a melting point in the neighborhood of 220° F. The heater 212 is operated to maintain the upper portion of the container 210 within the temperature range of from 230°–350° F. An additional bottom heater 218 is regulated through a control 220 connected thereto through a connecting wire 222 to maintain the lower portion of the container 210 within the temperature range of from 250°–350° F.

In accordance with this aspect of the invention, a polymer such as polyethylene or polypropylene is added to the container 210 and is then heated from 10 to 12 hours whereafter a leather scent or aroma imparting material containing a mixture defined thusly:

"A": At least one substance having the structure:

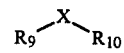

in an amount of from about 1% up to about 5% wherein $R_9$ represents $C_9$–$C_{11}$ straight-chain alkyl and wherein $R_{10}$ represents methyl and X is a moiety selected from the group consisting of:

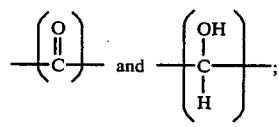

"B": At least one compound having the structure:

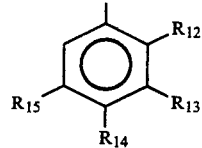

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

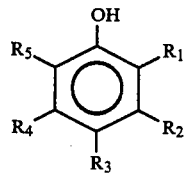

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

"A": At least one substance having the structure:

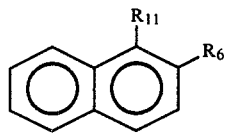

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

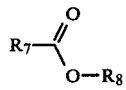

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

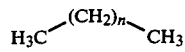

in an amount of from about 20% up to about 60% wherein n represents an integer of from 8 up to 28;

"G": Optionally, the compound having the structure:

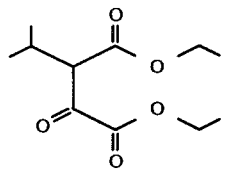

in an amount of from 0 up to about 6%; and

"H": Optionally, the compound having the structure:

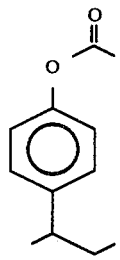

in an amount of from 0 up to about 6% with the requirement that:

$$\Sigma[A + B + C + D + E + F + G + H]$$

equal 100% is quickly added to melt. The material must be compatible with the polymer and forms a homogeneous liquid melt therewith. The heat resisting mixture generally containing about 10–40% by weight of a mixture included in the genus:

"A": At least one substance having the structure:

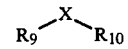

in an amount of from about 1% up to about 5% wherein $R_9$ represents $C_9$-$C_{11}$ straight-chain alkyl and wherein $R_{10}$ represents methyl and X is a moiety selected from the group consisting of:

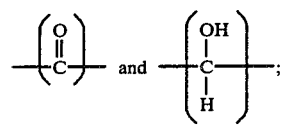

"B": At least one compound having the structure:

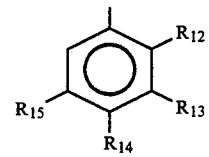

in an amount of from about 3 up to about 7% wherein each of $R_{12}$-$R_{15}$ represents hydrogen or $C_1$-$C_4$ alkyl with the proviso that at least two of $R_{12}$-$R_{15}$ represents hydrogen;

"C": At least one compound having the structure:

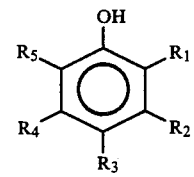

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl;

"D": Optionally, at least one compound having the structure:

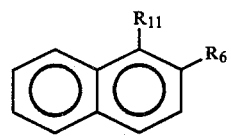

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

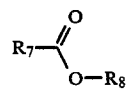

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

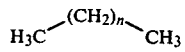

in an amount of from about 20% up to about 60% wherein n represents an integer of from 8 up to 28;

"G": Optionally, the compound having the structure:

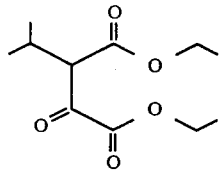

in an amount of from 0 up to about 6%; and

"H": Optionally, the compound having the structure:

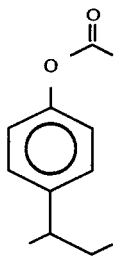

in an amount of from 0 up to about 6% with the requirement that:

$$\Sigma[A + B + C + D + E + F + G + H]$$

equal 100% is added to the polymer.

After the mixture included in the genus:

"A": At least one substance having the structure:

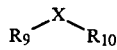

in an amount of from about 1% up to about 5% wherein $R_9$ represents $C_9$-$C_{11}$ straight-chain alkyl and wherein $R_{10}$ represents methyl and X is a moiety selected from the group consisting of:

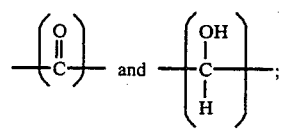

"B": At least one compound having the structure:

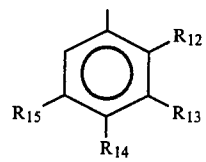

in an amount of from about 3 up to about 7% wherein each of $R_{12}$-$R_{15}$ represents hydrogen or $C_1$-$C_4$ alkyl with the proviso that at least two of $R_{12}$-$R_{15}$ represents hydrogen;

"C": At least one compound having the structure:

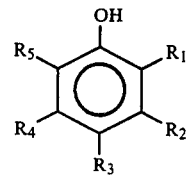

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl;

"D": Optionally, at least one compound having the structure:

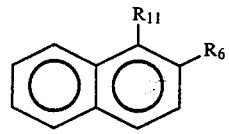

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"B": At least one compound defined according to the structure:

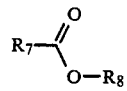

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

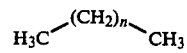

in an amount of from about 20% up to about 60% wherein n represents an integer of from 8 up to 28;

"G": Optionally, the compound having the structure:

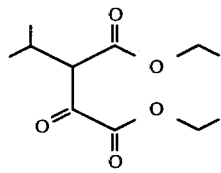

in an amount of from 0 up to about 6%; and

"H": Optionally, the compound having the structure:

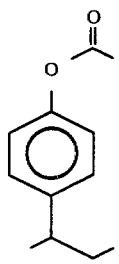

in an amount of from 0 up to about 6%
with the requirement that:

$$\Sigma[A + B + C + D + E + F + G + H]$$

equal 100% is added to container 210 the mixture is stirred for a few minutes, for example 5–15 minutes and maintained within the temperature range as indicated previously by the heating coils 212 and 218, respectively. The controls 216 and 220 are connected through cables 224 and 226 through a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and substance containing a mixture included within the genus, "A": At least one substance having the structure:

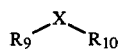

in an amount of from about 1% up to about 5% wherein $R_9$ represents $C_9$–$C_{11}$ straight-chain alkyl and wherein $R_{10}$ represents methyl and X is a moiety selected from the group consisting of:

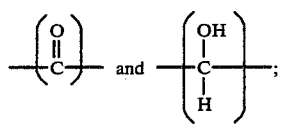

"B": At least one compound having the structure:

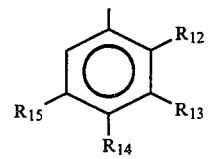

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

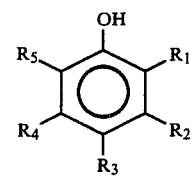

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

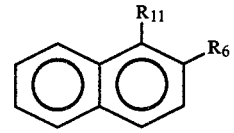

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

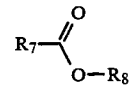

in an amount of from about 30% up to about 70% wherein $R_7$ represents $C_{11}$, $C_{13}$, or $C_{15}$ straight-chain alkyl and $R_8$ represents $C_1$–$C_3$ lower alkyl;

"F": At least one compound having the structure:

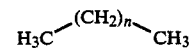

in an amount of from about 20% up to about 60% wherein n represents an integer of from 8 up to 28;

"G": Optionally, the compound having the structure:

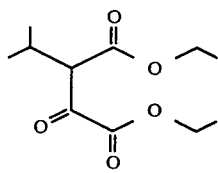

in an amount of from 0 up to about 6%; and

"H": Optionally, the compound having the structure:

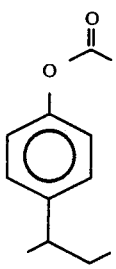

in an amount of from 0 up to about 6% with the requirement that:

$$\Sigma[A + B + C + D + E + F + G + H]$$

equal 100% will continuously drop through the orifice 234 downwardly from the conduit 232. During this time, the temperature of the polymer and a mixture included in the genus:

"A": At least one substance having the structure:

$$R_9 \overset{X}{\frown} R_{10}$$

in an amount of from about 1% up to about 5% wherein $R_9$ represents $C_9$-$C_{11}$ straight-chain alkyl and wherein $R_{10}$ represents methyl and X is a moiety selected from the group consisting of:

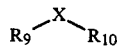

"B": At least one compound having the structure:

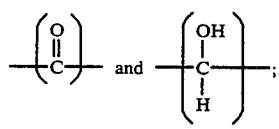

in an amount of from about 3 up to about 7% wherein each of $R_{12}$-$R_{15}$ represents hydrogen or $C_1$-$C_4$ alkyl with the proviso that at least two of $R_{12}$-$R_{15}$ represents hydrogen;

"C": At least one compound having the structure:

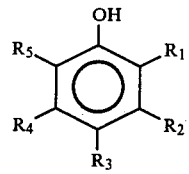

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl;

"D": Optionally, at least one compound having the structure:

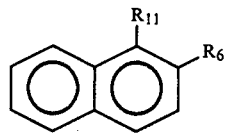

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

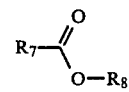

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

$$H_3C \overset{(CH_2)_n}{\frown} CH_3$$

in an amount of from about 20% up to about 60% wherein n represents an integer of from 8 up to 28;

"G": Optionally, the compound having the structure:

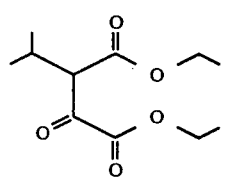

in an amount of from 0 up to about 6%; and

"H": Optionally, the compound having the structure:

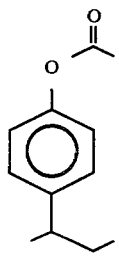

in an amount of from 0 up to about 6% with the requirement that:

$$\Sigma[A + B + C + D + E + F + G + H]$$

equal 100% in the container 210 as accurately controlled so that a temperature in the range of from 210° up to 275° F. will be maintained and the material exiting in the conduit 232. The regulation of the temperature through the control 216 and the control 220 is essential in order to insure temperature balance to provide for the continuous dropping or dripping of the molten polymer and a mixture included in the genus:

"A": At least one substance having the structure:

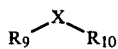

in an amount of from about 1% up to about 5% wherein $R_9$ represents $C_9$-$C_{11}$ straight-chain alkyl and wherein $R_{10}$ represents methyl and X is a moiety selected from the group consisting of:

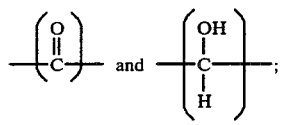

"B": At least one compound having the structure:

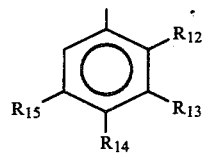

in an amount of from about 3 up to about 7% wherein each of $R_{12}$-$R_{15}$ represents hydrogen or $C_1$-$C_4$ alkyl with the proviso that at least two of $R_{12}$-$R_{15}$ represents hydrogen;

"C": At least one compound having the structure:

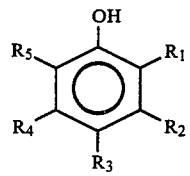

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl;

"D": Optionally, at least one compound having the structure:

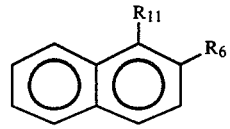

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

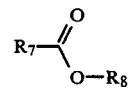

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

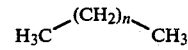

in an amount of from about 20% up to about 60% wherein n represents an integer of from 8 up to 28;

"G": Optionally, the compound having the structure:

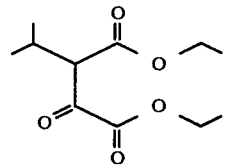

in an amount of from 0 up to about 6%; and

"H": Optionally, the compound having the structure:

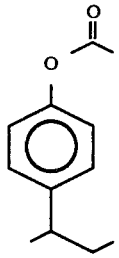

in an amount of from 0 up to about 6% with the requirement that:

$$\Sigma[A + B + C + D + E + F + G + H]$$

equal 100% or mixture containing same through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment.

A feature of the invention is the provision for moistening the conveyor belt 238 to insure the rapid formation of the solid polymer-leather scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

The present invention provides a mixture of compounds covered by the genus:

"A": At least one substance having the structure:

$$R_9 \diagdown X \diagdown R_{10}$$

in an amount of from about 1% up to about 5% wherein $R_9$ represents $C_9$–$C_{11}$ straight-chain alkyl and wherein $R_{10}$ represents methyl and X is a moiety selected from the group consisting of:

$$\left(\begin{matrix}O\\ \|\\ C\end{matrix}\right) \text{ and } \left(\begin{matrix}OH\\ |\\ C\\ |\\ H\end{matrix}\right);$$

"B": At least one compound having the structure:

[benzene ring with substituents $R_{12}$, $R_{13}$, $R_{14}$, $R_{15}$ and a methyl group]

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

[phenol ring with OH and substituents $R_1$, $R_2$, $R_3$, $R_4$, $R_5$]

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

[naphthalene ring with $R_{11}$ and $R_6$ substituents]

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

$$R_7-\overset{\overset{O}{\|}}{C}-O-R_8$$

in an amount of from about 30% up to about 70% wherein $R_7$ represents $C_{11}$, $C_{13}$, or $C_{15}$ straight-chain alkyl and $R_8$ represents $C_1$–$C_3$ lower alkyl;

"F": At least one compound having the structure:

$$H_3C-(CH_2)_n-CH_3$$

in an amount of from about 20% up to about 60% wherein n represents an integer of from 8 up to 28;

"G": Optionally, the compound having the structure:

[diketone ester structure]

in an amount of from 0 up to about 6%; and

"H": Optionally, the compound having the structure:

[phenyl ester with isopropyl group]

in an amount of from 0 up to about 6% with the requirement that:

$$\Sigma[A + B + C + D + E + F + G + H]$$

equal 100%.

The mixture of compounds defined according to:
"A": At least one substance having the structure:

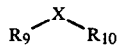

in an amount of from about 1% up to about 5% wherein $R_9$ represents $C_9-C_{11}$ straight-chain alkyl and wherein $R_{10}$ represents methyl and X is a moiety selected from the group consisting of:

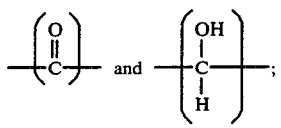

"B": At least one compound having the structure:

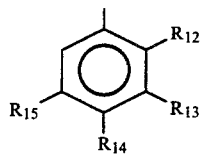

in an amount of from about 3 up to about 7% wherein each of $R_{12}-R_{15}$ represents hydrogen or $C_1-C_4$ alkyl with the proviso that at least two of $R_{12}-R_{15}$ represents hydrogen;

"C": At least one compound having the structure:

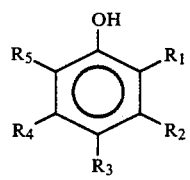

in an amount of from about 2% up to about 6% wherein $R_1$, $R_2$, $R_3$, $R_4$ and $R_5$ each represents hydrogen or $C_1-C_4$ alkyl with the proviso that one, two or three of $R_1$, $R_2$, $R_3$, $R_4$ and $R_5$ represents $C_1-C_4$ alkyl;

"D": Optionally, at least one compound having the structure:

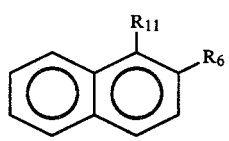

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

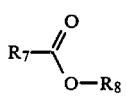

in an amount of from about 30% up to about 70% wherein $R_7$ represents $C_{11}$, $C_{13}$, or $C_{15}$ straight-chain alkyl and $R_8$ represents $C_1-C_3$ lower alkyl;

"F": At least one compound having the structure:

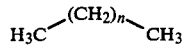

in an amount of from about 20% up to about 60% wherein n represents an integer of from 8 up to 28;

"G": Optionally, the compound having the structure:

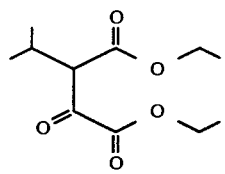

in an amount of from 0 up to about 6%; and

"H": Optionally, the compound having the structure:

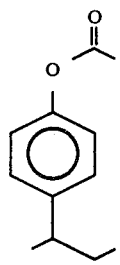

in an amount of from 0 up to about 6% with the requirement that:

$$\Sigma[A + B + C + D + E + F + G + H]$$

equal 100% is capable of augmenting, enhancing or imparting leathery aromas with spicy, ambery, caryophyllene-like, animalic, fruity, woody, ionone-like, sweet, vanillin-like, coconut, woody, orris, thyme-like and floral undertones and spicy, smooth leathery, oriental and sweet topnotes to perfume compositions, perfumed polymers (useful, for example, in synthetic leathers), perfumed articles (e.g. solid or liquid anionic, cationic, nonionic or zwitterionic detergents, fabric softener compositions, fabric softener articles, hair preparations, cosmetic powders and the like) and colognes.

Preferred members of the genus defined according to the structure:

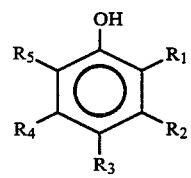

wherein $R_1$, $R_2$, $R_3$, $R_4$ and $R_5$ each represents hydrogen or $C_1-C_4$ alkyl with the proviso that 1, 2 or 3 of $R_1$, $R_2$, $R_3$, $R_4$ and $R_5$ represents $C_1-C_4$ alkyl are as follows:

TABLE I

| COMPOUND | PERFUMERY PROPERTY |
|---|---|
| 3-t-butylphenol | A leathery, spicy, ambery aroma. |
| 2,6-diisopropyl phenol | A spicy, leathery aroma. |
| 2,3-dimethyl phenol | A leathery, caryophyllene-like, animalic, spicy aroma. |
| 2,3,6-trimethyl phenol | A leathery, fruity, woody, $\beta$-ionone-like aroma with spicy and smooth leathery topnotes. |
| 2,5-dimethyl phenol | An animalic (tonquin musk-like), sweet, vanilla, spicy and coconut aroma profile. |
| 2-t-butylphenol | A leathery, animalic and smoky aroma with oriental, sweet and spicy topnotes. |
| 4-(2'butyl) phenol | A spicy, leathery aroma. |
| 2-n-propyl phenol | A balsamic, smoky aroma. |
| 3,5-dimethyl phenol | A woody, orris aroma. |
| 2,3,5-trimethyl phenol | A leathery, sweet, vanilla aroma. |
| 3,5-diisopropyl phenol | A spicy, thyme-like aroma. |
| 2,6-di-t-butylphenol | A leathery, woody, spicy aroma. |
| 2,4,6-trimethyl phenol | A leathery, woody, floral and spicy aroma profile. |
| 2-methyl-4-t-butylphenol | A leathery, spicy, woody and floral (jasmin) aroma with spicy, leathery topnotes. |
| 3-isopropyl phenol | An animalic, leathery aroma. |

Examples of the compounds defined according to the structure:

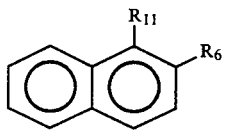

wherein $R_6$ represents hydrogen or methyl and $R_{11}$ represents hydrogen or methyl with the proviso that at least one of $R_6$ or $R_{11}$ is hydrogen are:
 Naphthalene;
 1-Methyl naphthalene; and
 2-Methyl naphthalene.

Examples of the compounds having the generic structure:

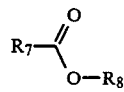

wherein $R_7$ represents $C_{11}$, $C_{13}$ or $C_{15}$ straight-chain alkyl and $R_8$ represents $C_1$–$C_3$ lower alkyl are:
 Isopropyl myristate;
 Methyl laurate;
 Methyl myristate; and
 Methyl palmitate.

Examples of the compounds having the generic structure:

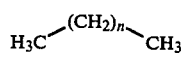

wherein n represents an integer of from 8 up to 28 are:
 n-Decane;
 n-Undecane;
 n-Tridecane;
 n-Tetradecane;
 n-Pentadecane;
 n-Hexadecane;
 n-Heptadecane;
 n-Octadecane;
 n-Nonadecane;
 Eicosane;
 Heneicosane;
 Docosane; and
 Tricosane.

Examples of the compound having the generic structure:

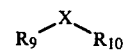

wherein $R_9$ represents $C_9$–$C_{11}$ alkyl and $R_{10}$ is methyl are:
 Methyl nonyl ketone;
 2-Tridecanone; and
 2-Tridecanol.

Examples of compounds having the generic structure:

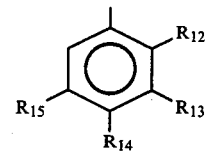

wherein $R_{12}$, $R_{13}$, $R_{14}$ and $R_{15}$ each represents hydrogen or $C_1$–$C_4$ lower alkyl with the proviso that at least 2 of $R_{12}$, $R_{13}$, $R_{14}$ and $R_{15}$ represents hydrogen are as follows:
 Xylene;
 Diethyl benzenes;
 1,2,4-Trimethyl benzene;
 1,2,3-Trimethyl benzene;
 4-t-Butyl toluene.

The compound having the structure:

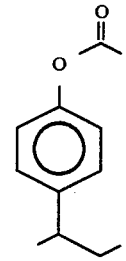

has an excellent, long-lasting leathery, ylang aroma with sweet floral topnotes.

The compound having the structure:

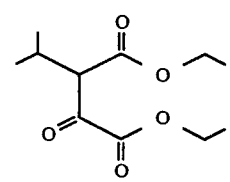

has a refined leathery and castoreum aroma profile.

The 4(2'-butyl) phenyl acetate having the structure:

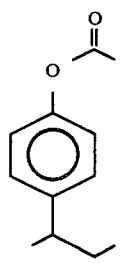

may be prepared from the corresponding phenol having the structure:

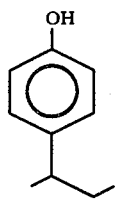

by acetylation thereof under standard esterification conditions using acetic anhydride according to the reaction;

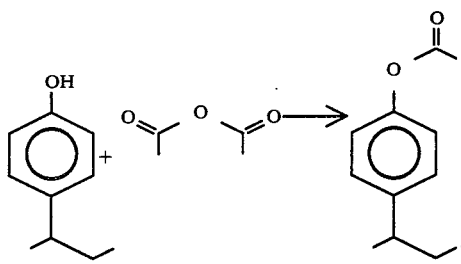

The reaction preferably takes place at reflux conditions in the presence of an inert solvent such as toluene. At the end of the reaction the reaction mass is neutralized and the reaction product is distilled at a temperature in the range of 75°–79° C. and 0.8–2 psi (absolute).

The compound having the structure:

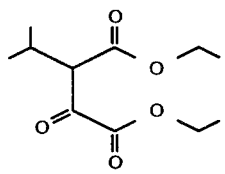

is a known compound disclosed at Chemical Abstracts Volume 99, Monograph 139339e (abstract of Japanese Kokai Tokkyo Koho No. 58/94042; J. Am. Chem. Soc. 72, 1352-6 (1950); and Acta Chem. Scand. 5, 485-6 (1951).

The diethyl ester of 2-isopropyl-3-oxosuccinic acid may be prepared by reacting ethyl isovalerate having the structure:

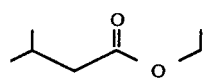

with diethyl oxalate according to the reaction:

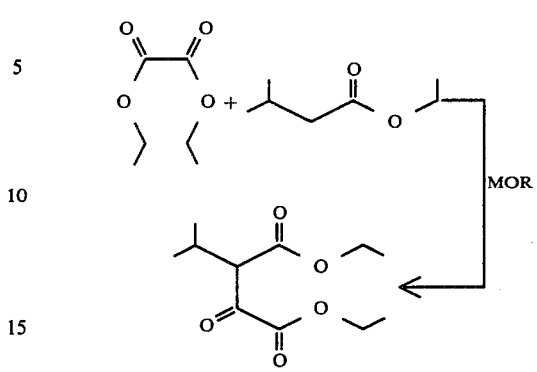

in the presence of an alkali metal alkoxide wherein M represents alkali metal such as sodium and potassium and R represents alkyl such as methyl, ethyl and isopropyl. The diethyl ester of 2-isopropyl-3-oxosuccinic acid of our invention having the structure:

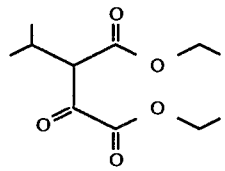

and the method for synthesizing same are well known in the prior art, set forth, supra.

The mixture of our invention defined as follows:

"A": At least one substance having the structure:

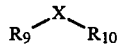

in an amount of from about 1% up to about 5% wherein $R_9$ represents $C_9$–$C_{11}$ straight-chain alkyl and wherein $R_{10}$ represents methyl and X is a moiety selected from the group consisting of:

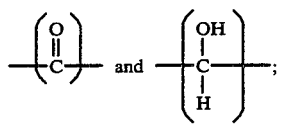

"B": At least one compound having the structure:

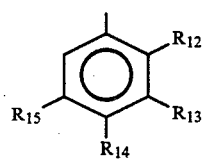

in an amount of from 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

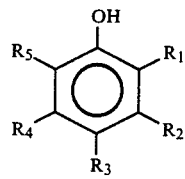

in an amount of from about 2% up to about 6% wherein $R_1$, $R_2$, $R_3$, $R_4$ and $R_5$ each represents hydrogen or $C_1$-$C_4$ alkyl with the proviso that one, two or three of $R_1$, $R_2$, $R_3$, $R_4$ and $R_5$ represents $C_1$-$C_4$ alkyl;

"D": Optionally, at least one compound having the structure:

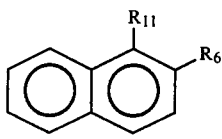

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

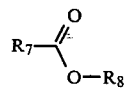

in an amount of from about 30% up to about 70% wherein $R_7$ represents $C_{11}$, $C_{13}$, or $C_{15}$ straight-chain alkyl and $R_8$ represents $C_1$-$C_3$ lower alkyl;

"F": At least one compound having the structure:

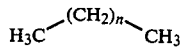

in an amount of from about 20% up to about 60% wherein n represents an integer of from 8 up to 28;

"G": Optionally, the compound having the structure:

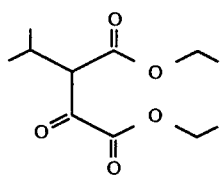

in an amount of from 0 up to about 6%; and

"H": Optionally, the compound having the structure:

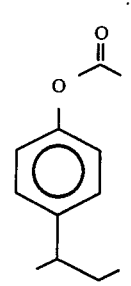

in an amount of from 0 up to about 6% with the requirement that:

$$\Sigma[A + B + C + D + E + F + G + H]$$

equal 100% (hereinafter referred to as "the mixture of our invention") and one or more auxiliary perfume ingredients including, for example, alcohols (other than the phenols of the mixture of our invention), aldehydes, ketones (other than the ketones of our invention), terpinic hydrocarbons, nitriles, esters (other than the esters of our invention), lactones, natural essential oils and synthetic essential oils, may be admixed so that the combined odors of the individual components produce a pleasant and desired leathery fragrance, for example, those useful in causing leather-like textile materials to have an intense, long-lasting leather aroma, e.g., those described in U.S. Pat. No. 4,465,730 issued on Aug. 14, 1984, the specification for which is incorporated by reference herein.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the overall sensory effect of the perfume composition will be at least the sum total of the effects of each of the ingredients. Thus, the mixtures of our invention can be used to alter, modify or enhance the leather aroma characteristics of a perfume composition, for example, by utilizing or moderating the olfactory reaction contributed by another ingredient in the composition.

The amount of mixtures of our invention which will be effective in leathery perfume compositions as well as in leathery perfumed articles and leathery colognes depends on many factors including the other ingredients, their amounts and the effects which are desired. It has been found that leathery perfume compositions containing as little as 0.1% of the mixtures of our invention can be used to impart, augment or enhance leathery aromas with spicy, ambery, caryophyllene-like, animalic, tonquin-musk-like, sweet, vanilla-like, coconut, woody, orris, thyme-like, floral, fruity, $\beta$-ionone-like undertones with spicy and smooth leathery, oriental and sweet topnotes to soaps, cosmetics, polymers of other products. The amount employed can range up to 100% of the fragrance components and will depend on considerations of cost, nature of the end product, the effect desired and the finished product and the particular fragrance sought.

The mixtures of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens, powders such as talcs, dusting powders, face powders and the like. When used as (an) olfactory component(s) as little as 0.1% of the mixtures of our invention will suffice to impart an intense leathery note to perfume formulations including woody and rose formulations but also including leather formulations. Generally, no more than 5% of the mixtures of our invention based on the ultimate end product is required in the perfumed article. Accordingly, the perfumed article of our invention may contain from about 0.1% up to about 5% by weight of the perfumed article.

In addition, the perfume composition or fragrance composition of our invention can contain a vehicle or carrier for the mixture of our invention. The vehicle can be a liquid such as an alcohol, a non-toxic glycol or the like. The carrier can also be an absorbent solid such as gum (e.g., gum arabic, guar gum or xanthan gum) or components for encapsulating the composition (such as gelatin when encapsulating by means of coacervation or such as a urea formaldehyde prepolymer when encapsulating forming a urea formaldehyde polymer wall around a liquid perfume center).

The mixture of our invention may be blended into polymers when forming a perfumed polymer by means of extrusion using a single or double screw extruder or techniques such as that set forth in U.S. Pat. No. 4,427,498 issued on Jan. 27, 1981, the disclosure of which is incorporated by reference herein, which discloses microporous polymers which are capable of containing volatile substance such as perfumes and the like and forms ranging from films to blocks and intricate shapes from synthetic thermoplastic polymers such as olefinic condensation or oxidation polymers.

Other techniques of blending the mixtures of our invention with polymers are exemplified in U.S. Pat. No. 3,505,432 (the specification for which is incorporated by reference herein) which discloses a method for scenting a polyolefin with such materials as the mixtures of our invention which comprises:

(a) mixing a first amount of the liquid polyolefin (e.g., polyethylene or polypropylene) with a relatively large amount of leather scent-imparting material (in this case the mixtures of our invention) to form a flowable mass;
(b) forming drops of said mass and causing substantially instantaneous solidification of said drops into polyolefin pellets having a relatively large amount of such scent-imparting materials as the mixtures of our invention imprisoned therein;
(c) melting said pellets with a second amount of polyolefin and said second amount being larger than the first amount; and
(d) solidifying the melt of (c).

The following Examples I, II and III set forth methods for ascertainment of actual natural components in leather aroma existing in natural leathers or in the head space above the natural leathers (Example III). Examples IV and V set forth syntheses for the products having the structures:

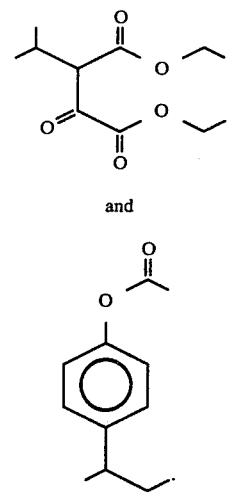

and

Examples following Example V, that is Examples VI, et seq, set forth examples indicating organoleptic utilities of the mixtures of our invention.

It will be understood that these examples are illustrative and that the invention is not to be restricted thereto except as indicated in the appended claims.

EXAMPLE I

CHEMICAL EXTRACTION OF VEGETABLE-TANNED LEATHER

330 Grams of sliced leather pieces (measuring approximately 1"×½") are placed in a large Soxhlet extractor and extracted with 3 liters of diethyl ether. The ether extracted leather is then reextracted with 3 liters of FREON® 11 for eight hours. After removal of solvent from the first extract, 8.5 grams of a crude extract results. After removal of the FREON® 11, no extract results.

The extract is then distilled on a short path micro distillation column to yield four fractions as follows:

| FRACTION NO. | VAPOR TEMP. (°C.) | LIQUID TEMP. (°C.) | VACUUM mm/Hg. PRESSURE | WEIGHT OF FRACTION (gms) |
| --- | --- | --- | --- | --- |
| 1 | 97/112 | 159/162 | 1.0/1.0 | 0.05 |
| 2 | 117 | 165 | 1.0 | 0.05 |
| 3 | 128 | 170 | 1.0 | 0.40 |
| 4 | 126 | 175 | 1.0 | 0.40 |

FIG. 1 is the GLC profile of the crude extract prior to distillation (Conditions: SE-30 glass capillary column, 50 M×0.032" programmed at 80°–220° C. at 2° C. per minute).

The peak indicated by reference numeral 10 is the peak for n-octadecane.

The peak indicated by reference numeral 11 is the peak for n-heptadecane.

The peak indicated by reference numeral 12 is the peak for nonadecane.

The peak indicated by reference numeral 13 is the peak for n-eicosane.

The peak indicated by reference numeral 14 is the peak for methyl myristate.

The peak indicated by reference numeral 15 is the peak for methyl palmitate.

The peak indicated by reference numeral 16 is the peak for methyl stearate.

The peak indicated by reference numeral 17 is the peak for methyl octadecenoate.

Figure 5:
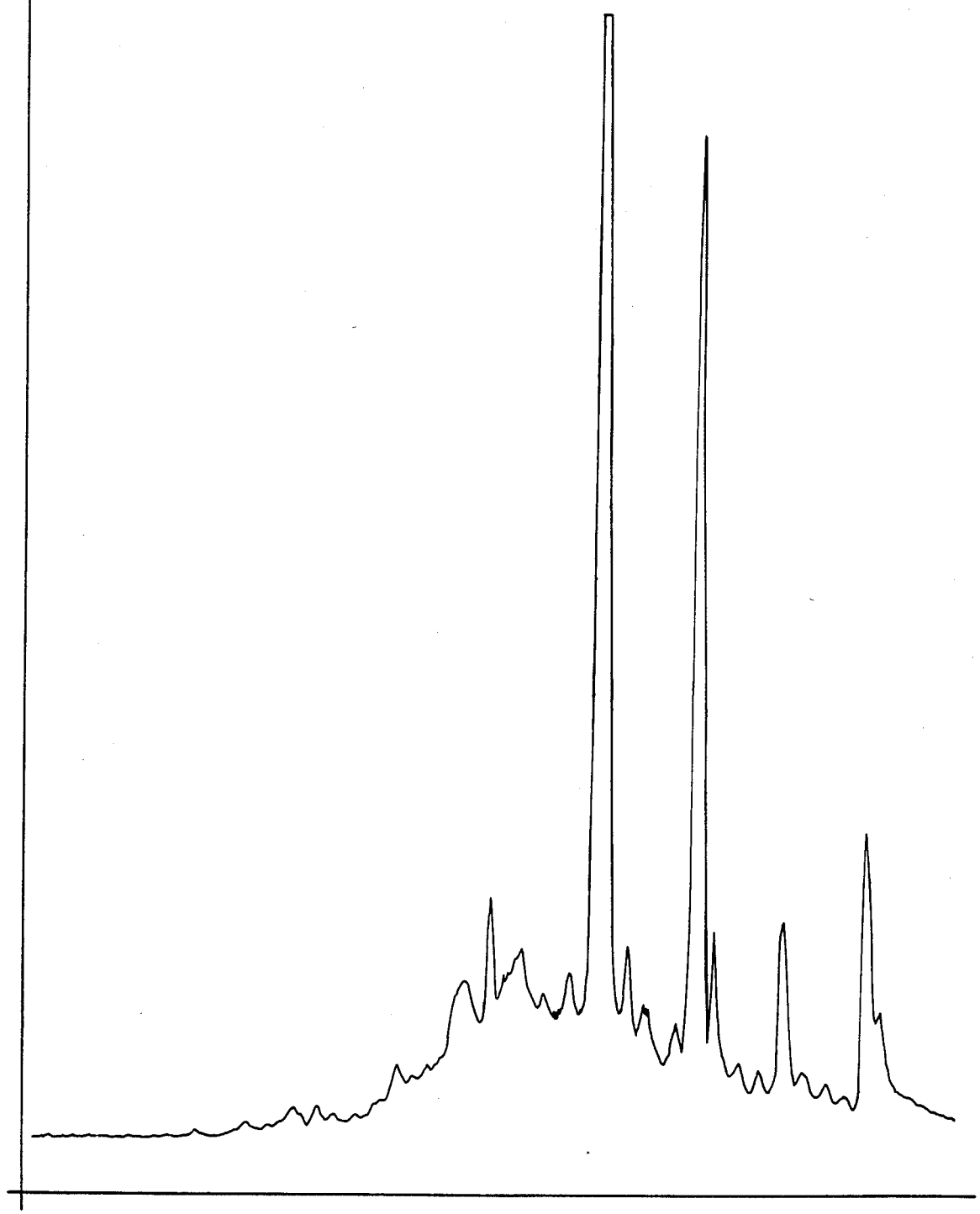
FIG. 5 is the GLC profile for distillation fraction 4 of the distillation product of the extract of Example I (Conditions: 2.5'×0.125" 5% carbowax column programmed at 100°-220° C. at 6° C. per minute).

FIG. 5 is the GLC profile for fraction 4 of the foregoing distillation.

The standard analytical technique for analyzing the extract is set forth in the following diagram:

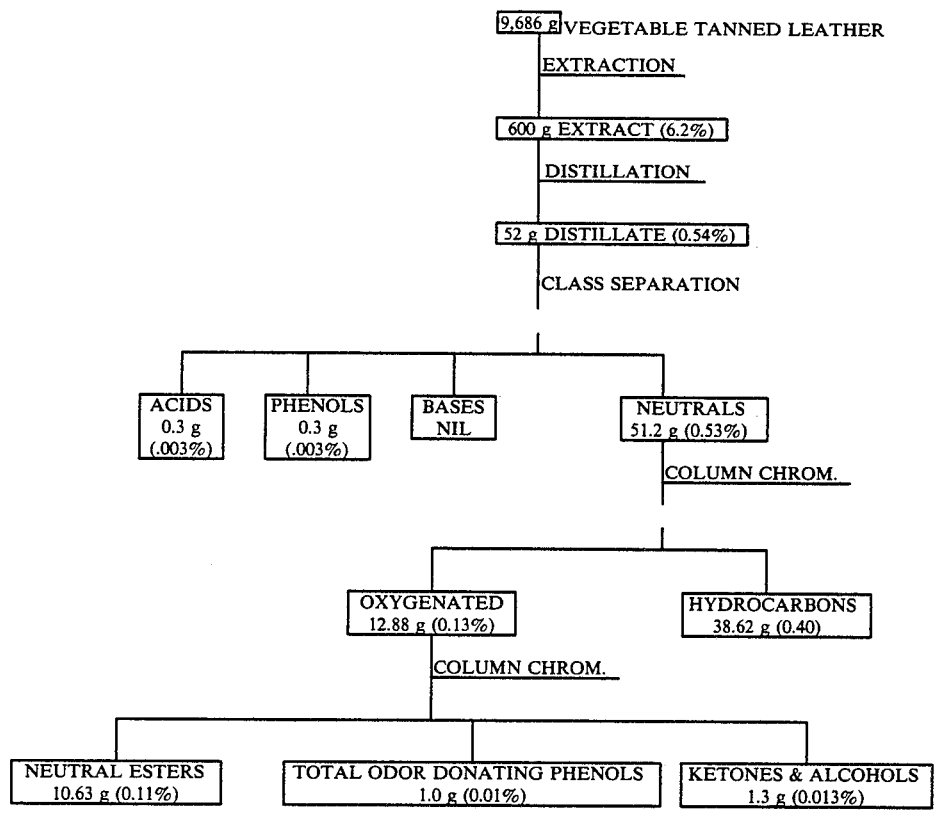

Figure 2:
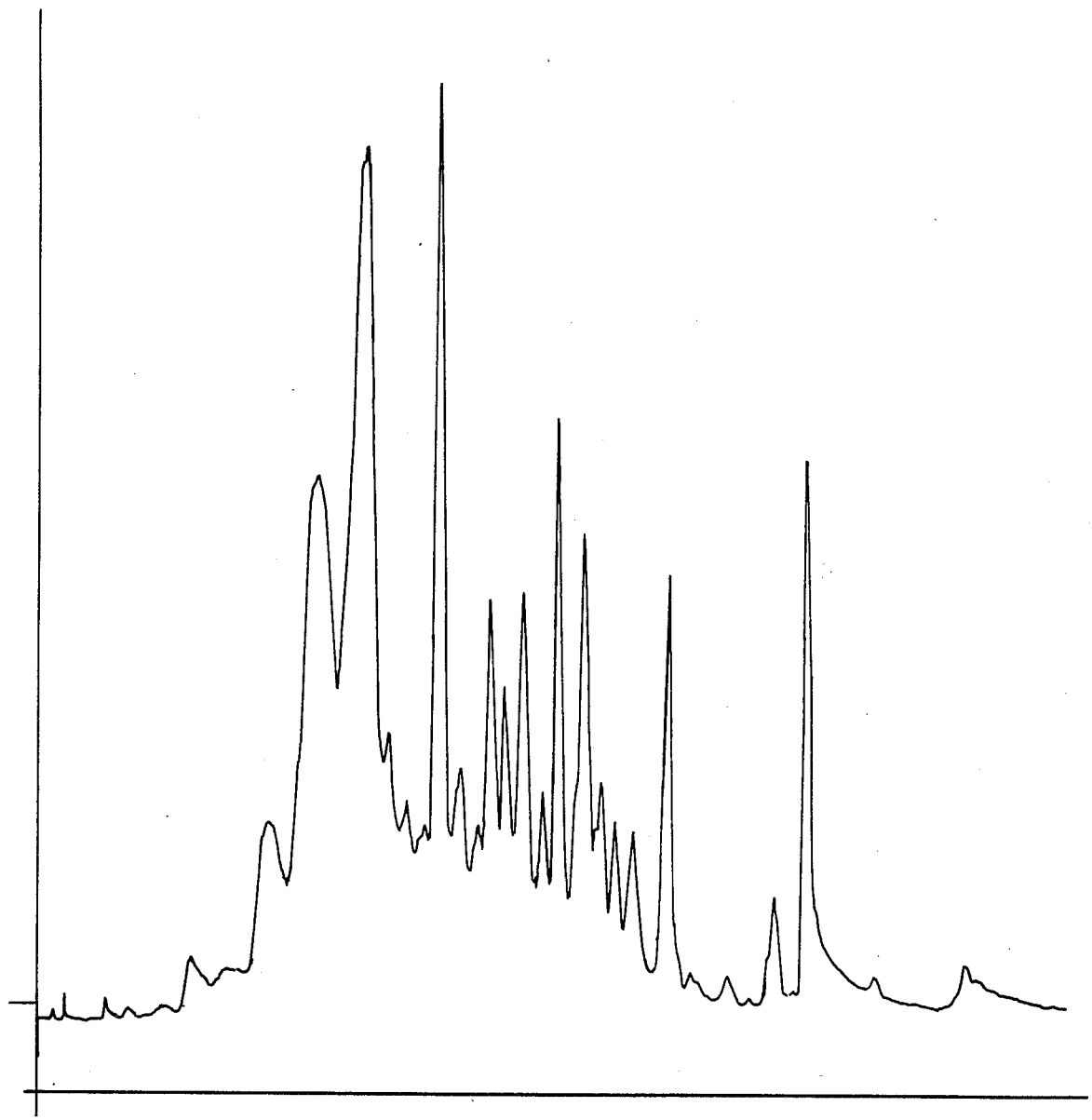
FIG. 2 is the GLC profile for distillation fraction 1 of the distillation of the extract of Example I (Conditions: 2.5'×0.125" 5% carbowax column programmed at 100°-220° C. at 6° C. per minute).

FIG. 2 is the GLC profile for fraction 1 of the foregoing distillation (Conditions: 2.5'×0.125"5% carbowax column programmed at 100°–220° C. at 6° C. per minute).

Figure 3:
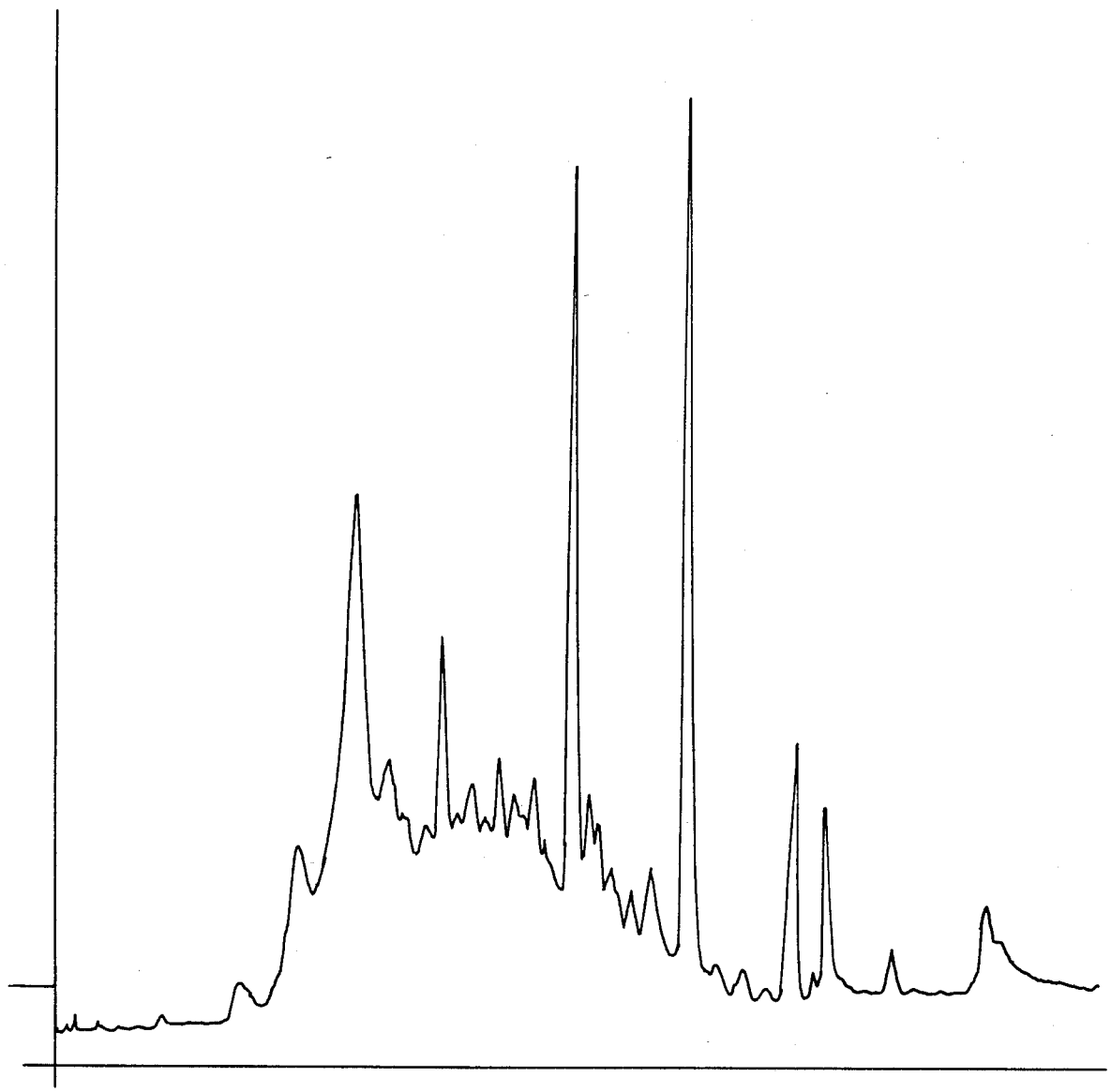
FIG. 3 is the GLC profile for distillation fraction 2 of the distillation product of the extract of Example I (Conditions: 2.5'×0.125" 5% carbowax column programmed at 100-220° C. at 6° C. per minute).

FIG. 3 is the GLC profile for fraction 2 of the foregoing distillation.

Figure 4:
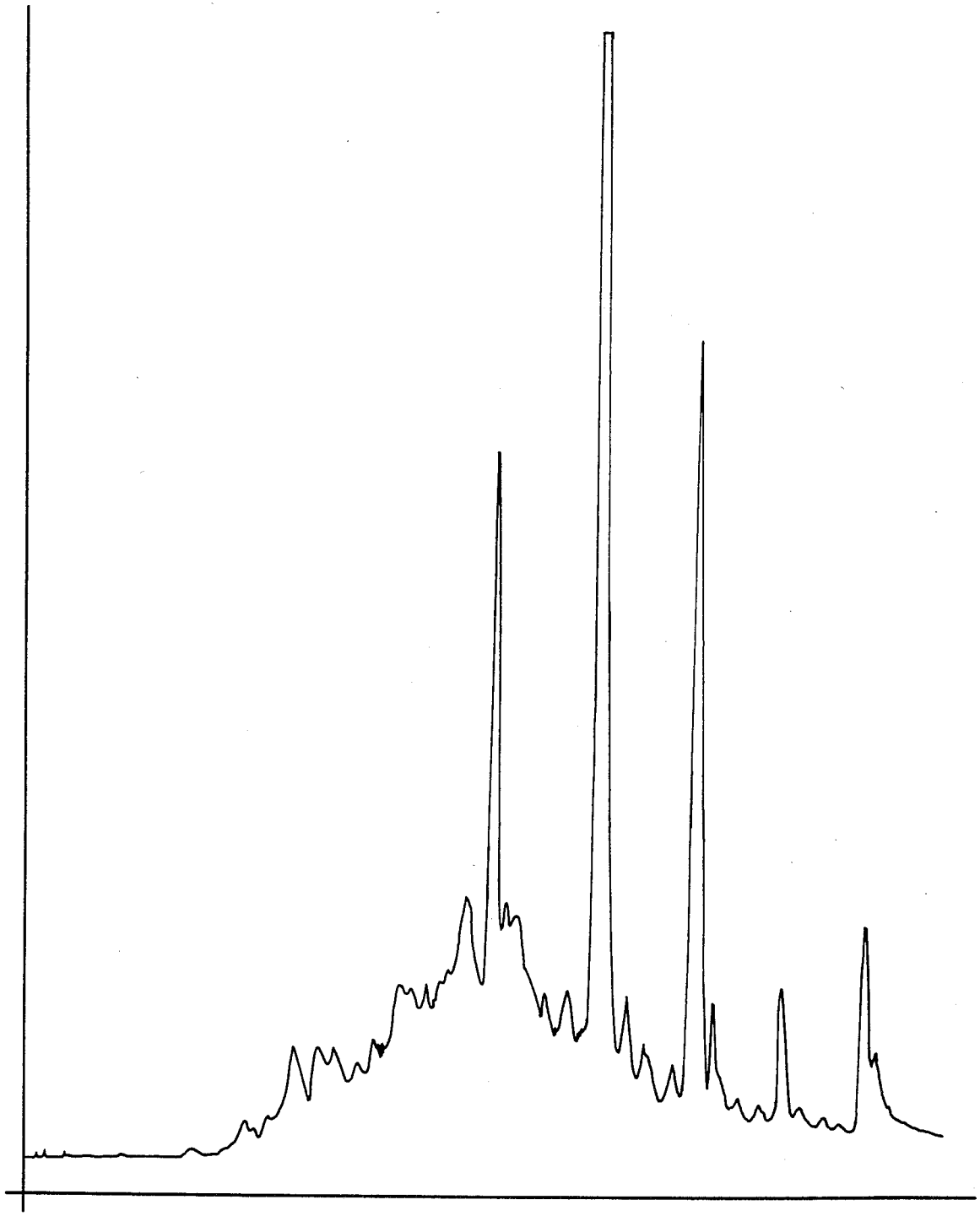
FIG. 4 is the GLC profile for distillation fraction 3 of the distillation product of the extract of Example I (Conditions: 2.5'×0.125" 5% carbowax column programmed at 100°-220° C. at 6° C. per minute).

FIG. 4 is the GLC profile for fraction 3 of the foregoing distillation.

EXAMPLE II

ANALYSIS OF VEGETABLE-TANNED LEATHER 52.1 Grams of leather extract distillate is prepared by the same procedure as Example I (117°–128° C. at 1.0 mm/Hg. pressure boiling point).

Half of this material was then subjected to class separation using techniques known in the art as follows:

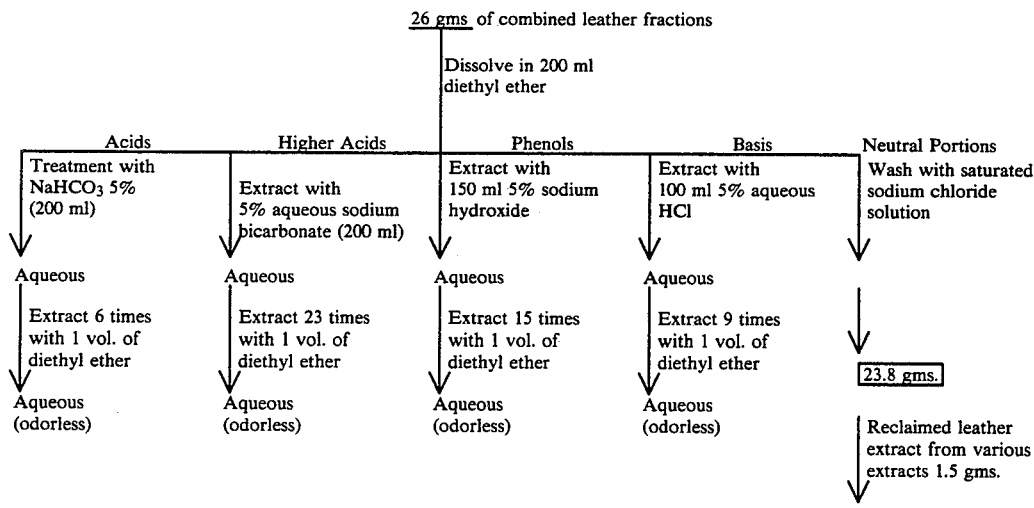

| Acidify using 100 ml 10% Aqueous HCl Extract 4 times with 1 vol. of ether each time | Acidify with 10% aqueous HCl (100 ml) Extract 4 times with 1 vol. of ether each time | Acidify with 100 ml 10% aqueous HCl; then extract 4 times with 1 vol. of diethyl ether each time | Add 75 ml N sodium hydroxide; then extract 4 times with 1 vol. of diethyl ether each time |
|---|---|---|---|
| (Trace) | (Trace) | (Trace) | (Less than a Trace) |

All extracts are dried over anhydrous magnesium sulfate and the solvent is removed by room temperature rotary vacuum evaporation.

The resulting odor evaluation is as follows:

(i) lower acids: phenyl acedic acid-like animal-like, green, slightly leathery;
(ii) higher acids: some leather character; has some sweet benzoin and is vanilla-like;
(iii) phenols: phenolic birch-tar, and clove terpine-like;
(iv) basis: pyridine like;
(v) neutral portion: oily, leathery solventy somewhat of a salicylate note but intensely leathery.

The neutral portion is column chromatographed to determine the various components therein. The column chromatographed diagram is as follows:

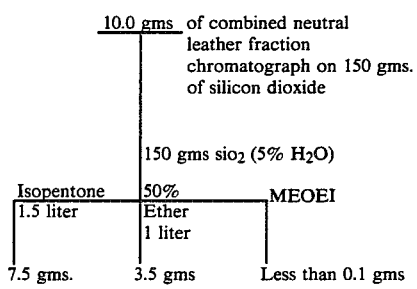

The isopentane eluate and 50% diether eluate are odor evaluated. The 50% ether eluate has a more distinct leathery aroma than the isopentane eluate but on dry-out the isopentane eluate is leathery.

To isolate the chemical compounds responsible for the leather odor in the 50% ether eluate, the following chromatographic procedure is performed as set forth in the following diagram:

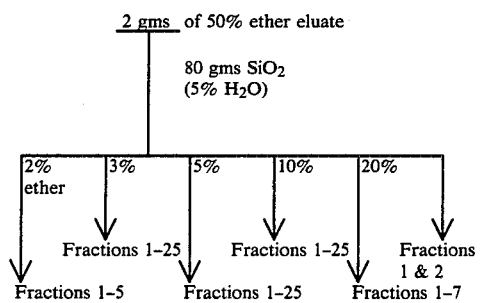

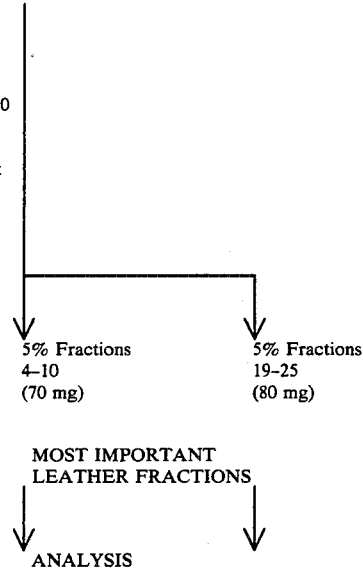

Each fraction (89) contained approximately 20–30 mg of material. Many fractions that were analytically the same were combined.

5% Fractions 4–10 (70 mg)

5% Fractions 19–25 (80 mg)

MOST IMPORTANT LEATHER FRACTIONS

ANALYSIS

FIG. 6A is the GLC profile for distillation fraction 4–10 prior to chromatographic separation (Conditions: carbowax fused silica programmed at 60°–220° C. at 2° C. per minute).

The peak indicated by reference numeral 100 is the peak for 2,6-di-t-butyl-4-methyl phenol.

The peak indicated by reference numeral 101 is the peak for 2-methyl phenol.

The peak indicated by reference numeral 102 is the peak for 2,3,6-trimethyl phenol.

The peak indicated by reference numeral 103 is the peak for 2,4,6-trimethyl phenol.

The peak indicated by reference numeral 104 is the peak for 2-n-propyl phenol admixed with 2,3-dimethyl phenol.

The peak indicated by reference numeral 105 is the peak for 3,5-dimethyl phenol.

The peak indicated by reference numeral 106 is the peak for 2,3,5-trimethyl phenol.

The peak indicated by reference numeral 107 is the peak for 2-t-butyl-4-methyl phenol.

The peak indicated by reference numeral 108 is the peak for 3,5-diisopropyl phenol.

The peak indicated by reference numeral 109 is the peak for 2-chloro phenol admixed with 4-chloro phenol.

FIG. 6B is the GLC profile for distillation fractions 19–25 prior to chromatographic separation (Conditions: Carbowax fused silica column programmed at 60°–220° C. per minute).

The peak indicated by reference numeral 120 is the peak for 3-methyl phenol.

The peak indicated by reference numeral 121 is the peak for 4-ethyl phenol.

The peak indicated by reference numeral 122 is the peak for 3-isopropyl-6-methyl phenol.

The peak indicated by reference numeral 123 is the peak for 2(4'-butyl) phenol.

The peak indicated by reference numeral 124 is the peak for 3,5-diisopropyl phenol.

The peak indicated by reference numeral 125 is the peak for the mixture of 3-chloro phenol and 4-chloro phenol.

FIG. 6C is the GLC profile for the phenolic section of the chromatographic eluate (first chromatograph) (Conditions: carbowax fused silica column programmed at 60°–220° C. at 2° C. per minute).

The peak indicated by reference numeral 30 is the peak for 2-methyl phenol.

The peak indicated by reference numeral 31 is the peak for 2,6-di-t-butyl-4-methyl phenol.

The peak indicated by reference numeral 32 is the peak for the mixture of 2-methyl phenol and 2,4,6-trimethyl phenol.

The peak indicated by reference numeral 33 is the peak for 2,6-di-t-butylphenol.

The peak indicated by reference numeral 34 is the peak for 4-methyl phenol.

The peak indicated by reference numeral 35 is the peak for 3-methyl phenol.

The peak indicated by reference numeral 36 is the peak for 4-ethyl phenol admixed with 3,5-dimethyl phenol.

The peak indicated by reference numeral 37 is the peak for 3-ethyl phenol.

The peak indicated by reference numeral 38 is the peak for the mixture of 2,3,5-trimethyl phenol and 3,4-dimethyl phenol.

The peak indicated by reference numeral 39 is the peak for 4(2'-butyl) phenol.

The peak indicated by reference numeral 40 is the peak for 2-isopropyl-5-methyl phenol.

The peak indicated by reference numeral 41 is the peak for 3-methyl-4-t-butylphenol.

The peak indicated by reference numeral 42 is the peak for 4-isopropyl phenol.

The peak indicated by reference numeral 43 is the peak for 3,5-diisopropyl phenol.

The peak indicated by reference numeral 44 is the peak for 2,3,6-trimethyl phenol.

The peak indicated by reference numeral 45 is the peak for 2-ethyl phenol.

The peak indicated by reference numeral 50 is the peak for β-naphthol.

EXAMPLE III

ANALYSIS OF HEAD SPACE (ISOLATION AND IDENTIFICATION OF THE VOLATILES OF LEATHER)

2.5 Pounds of vegetable-tanned leather is purchased from the Tandy Leather Store: 19-E Front Street, Red Bank, N.J. 07760.

The material is rolled into a tight cylindrical roll and then purged in the standard head space apparatus used in the analysis of fresh air dried cloth (Reference: U.S. Pat. No. 4,434,086 issued on Feb. 28, 1984 the specification for which is incorporated by reference herein).

The resulting leather is purged with nitrogen for a period of three days at 23° C. Analysis by G. C./M. S. identifies the following materials:

(i) toluene;
(ii) 3 isomers of di-methyl phenol;
(iii) nonane;
(iv) 5 isomers of tri-methyl phenol;
(v) 2 isomers of chloro toluene;
(vi) 2 isomers of di-chloro benzene;
(vii) 1-methyl-4-isopropenyl cyclohexene;
(viii) allyl benzene;
(xi) 7 isomers of di-ethyl benzene;
(x) methyl isopropenyl benzene;
(xi) naphthalene;
(xii) 4 isomers of methyl-t-butyl benzene;
(xiii) benzothiazole;
(xiv) $C_9$–$C_{14}$ straight chain hydrocarbons;
(xv) 3 isomers of dimethyl indane;
(xvi) 2 isomers of methyl naphthalene;
(xvii) acenaphthene;
(xxviii) diphenyl;
(xix) α-cedrene;
(xxi) 2,6-di-t-butyl-4-methyl phenol.

FIG. 7 is the GLC profile for the resulting head space (Conditions: 400' OV-1 column programmed at 60°–190° C. at 2° C. per minute.

The peak indicated by reference numeral 70 is the peak for toluene.

The peak indicated by reference numeral 71 is the peak for 1,3,4-trimethyl benzene.

The peak indicated by reference numeral 72 is the peak for n-decane.

The peak indicated by reference numeral 73 is the peak for diethyl benzenes.

The peak indicated by reference numeral 74 is also the peak for diethyl benzenes.

The peak indicated by reference numeral 75 is the peak for naphthalene.

The peak indicated by reference numeral 76 is the peak for the silicone resin.

The peaks indicated by reference numerals 77A and 77B are the peaks for methyl naphthalenes.

The peak indicated by reference numeral 78 is the peak for n-tridecane.

The peak indicated by reference numeral 79 is the peak for acenaphthene.

The peak indicated by reference numeral 80 is the peak for diphenyl oxide.

The peak indicated by reference numeral 81 is the peak for n-tetradecane.

The peak indicated by reference numeral 82 is the peak for thujopsane.

The peak indicated by reference numeral 83 is the peak for 2,6-di-t-butyl-4-methyl phenol.

EXAMPLE IV

PREPARATION OF 4(2'-BUTYL) PHENYL ACETATE

Reaction

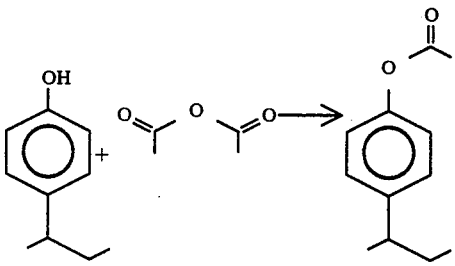

Into a 1 liter reaction flask equipped with stirrer, thermometer, reflux condenser, addition funnel and heating mantle is placed 150 grams of 4(2'-butyl) phenol in 200 ml toluene. The reaction mass with stirring is heated to reflux and while refluxing, dropwise over a period of one hour, 122 grams of acetic anhydride (1.2 moles) is added to the reaction mass. After the one hour period, the reaction mass is refluxed for an additional one hour. The reaction mass is then cooled to room temperature and 100 ml water is added. The resulting mixture is heated to 60° C. for one hour with stirring.

The organic phase is separated from the aqueous phase and the organic phase is washed with concentrated salt solution followed by water followed by saturated sodium carbonate solution.

The organic phase is then dried over anhydrous magnesium sulfate and distilled on a 12" Goodloe column yielding the following fractions:

| FRACTION NO. | VAPOR TEMP. (°C.) | LIQUID TEMP. (°C.) | VACUUM PSI (ABSOLUTE) |
|---|---|---|---|
| 1 | 24/24 | 65/110 | 2/2 |
| 2 | 72/74 | 85/86 | 2/2 |
| 3 | 79 | 92 | 1.0 |
| 4 | 79 | 93 | 0.8 |
| 5 | 78 | 92 | 2.0 |
| 6 | 78 | 92 | 1.0 |
| 7 | 78 | 91 | 1.0 |
| 8 | 78 | 92 | 1.0 |
| 9 | 78 | 92 | 1.0 |
| 10 | 75 | 95 | 1.0 |
| 11 | 60 | 144 | 0.6 |
| 12 | 63 | 186 | 0.6 |

Bulked fractions 3-9 have excellent, long-lasting leathery and ylang aroma nuances with sweet, floral topnotes.

EXAMPLE V

PREPARATION OF DIETHYL ESTER OF 2-ISOPROPYL-3-OXOSUCCINIC ACID

Reaction

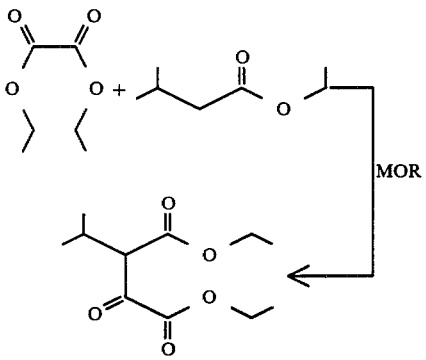

(wherein M represents sodium and R represents ethyl).

Into a 2 liter three necked reaction flask equipped with stirrer, thermometer, condenser, addition funnel and nitrogen inlet tube is placed 800 ml anhydrous toluene and 41 grams of sodium ethoxide. Over a period of 30 minutes from the addition funnel a mixture of 73 grams diethyl oxalate (0.5 moles) and 65 grams of ethyl valerate (0.5 moles) is added to the reaction mass while maintaining the reaction temperature at 35° C. At the end of the addition period, the reaction mass is heated to 50° C. and maintained at 50° C. with stirring for a period of 10 hours. At the end of the 10 hour period the reaction mass is cooled to room temperature and 300 ml water is added. The pH is adjusted to 6 using 5% aqueous hydrochloric acid (70 ml).

The organic phase is separated from the aqueous phase and the organic phase is washed with 400 ml water and then dried over anhydrous sodium sulphate. The organic phase is then concentrated on a rotary evaporator to 30 grams. The resulting product is distilled at 80° C. and 0.7 mm/hg yielding the diethyl ester of 2-isopropyl-3-oxosuccinic acid having the structure:

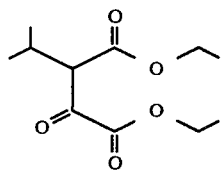

FIG. 8 is the GLC profile for the crude reaction product prior to distillation (conditions: 50M×0.32M fused silca capillary column coated with carbowax 20M programmed at 50°-225° C. at 2° C. per minute).

FIG. 9 is the NMR spectrum for the diethyl ester of 2-isopropyl-3-oxosuccinic acid having the structure:

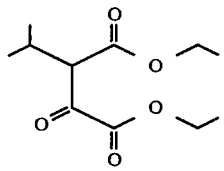

(Conditions: Field strength: 100 MHz; solvent: CFCl$_3$).

FIG. 10 is the GC-MS spectrum for the diethyl ester of 2-isopropyl-3-oxosuccinic acid having the structure:

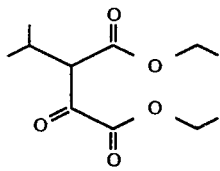

EXAMPLE VI(A)

LEATHER FRAGRANCE

The following leather fragrance is prepared:

| INGREDIENTS | WEIGHT PERCENT |
|---|---|
| Diethyl ester of 2-isopropyl-3-oxosuccinic acid having the structure: 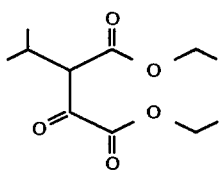 produced according to Example V | 3% |

-continued

| INGREDIENTS | WEIGHT PERCENT |
|---|---|
| Methyl nonyl ketone | 4% |
| 2-undecanol | 4% |
| m-xylene | 6% |
| 2,4-di-n-propyl phenol | 5% |
| Ethyl laurate | 40% |
| n-octane | 19% |
| n-dodecane | 19% |

The resulting perfume composition has an excellent leathery aroma with spicy, castoreum and tonquin musk-like undertones and spicy, smooth leathery topnotes.

EXAMPLE VI(B)

LEATHER FRAGRANCE

The following leather fragrance is prepared:

| INGREDIENTS | WEIGHT PERCENT |
|---|---|
| Methyl nonyl ketone | 4% |
| 2-Tridecanol | 2% |
| 2-Undecanol | 2% |
| m-Xylene | 6% |
| 2,3-Dimethyl phenol | 3% |
| 2,6-Diisopropyl phenol | 2% |
| Ethyl myristate | 23% |
| Ethyl laurate | 20% |
| n-Tridecane | 19% |
| n-Dodecane | 19% |

The resulting perfume composition has an excellent leathery aroma with spicy, caryophyllene-like, animalic undertones.

EXAMPLE VI(C)

LEATHER FRAGRANCE

The following leather fragrance is prepared:

| INGREDIENTS | WEIGHT PERCENT |
|---|---|
| Methyl nonyl ketone | 4% |
| 2-Undecanol | 2% |
| 2-Tridecanol | 1% |
| 2-Tetradecanol | 1% |
| Toluene | 3% |
| m-Xylene | 3% |
| 4-t-Butyl-2-methyl phenol | 5% |
| Ethyl myristate | 20% |
| Ethyl laurate | 23% |
| n-Octane | 19% |
| n-Dodecane | 19% |

The resulting aroma can be described as leathery with spicy, woody, floral (jasmin) undertones and spicy, leathery topnotes.

EXAMPLE VII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| SUBSTANCE | AROMA DESCRIPTION |
|---|---|
| Perfume composition of | A leathery aroma with spicy, |
| Example VI(A) | castoreum and tonquin musk-like undertones and spicy, smooth leathery topnotes. |
| Perfume composition of Example VI(B) | A leathery aroma with spicy, caryophyllene-like, animalic undertones. |
| Perfume composition of Example VI(C) | A leathery aroma with spicy, woody, floral (jasmin) undertones and spicy, leathery topnotes. |

EXAMPLE VIII

PERFUMED LIQUID DETERGENTS

Concentrated liquid detergents (lysine salt of n-dodecylbenzene sulfonic acid as more specifically described in U.S. Pat. No. 3,948,818, issued on April 6, 1976 incorporated by reference herein) with aroma nuances as set forth in Table II of Example VII, are prepared containing 0.10%, 0.15%, 0.20%, 0.25%, 0.30% and 0.35% of the substance set forth in Table II of Example VII. They are prepared by adding and homogeneously mixing the appropriate quantity of substance set forth in Table II of Example VII in the liquid detergent. The detergents all possess excellent aromas as set forth in Table II of Example VII, the intensity increasing with greater concentrations of substance as set forth in Table II of Example VII.

EXAMPLE IX

PREPARATION OF COLOGNES AND HANDKERCHIEF PERFUMES

Compositions as set forth in Table II of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VII are imparted to the colognes and to the handkerchief perfumes at all levels indicated.

EXAMPLE X

PREPARATION OF SOAP COMPOSITIONS

One hundred grams of soap chips (per sample) (IVORY ® produced by the Proctor & Gamble Company of Cincinnati, Ohio), are each mixed with one gram samples of substances as set forth in Table II of Example VII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VII.

EXAMPLE XI

PREPARATION OF SOLID DETERGENT COMPOSITIONS

Detergents are prepared using the following ingredients according to Example I of Canadian Patent No. 1,007,948 (incorporated by reference herein):

| INGREDIENT | PERCENT BY WEIGHT |
|---|---|
| Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is phosphate-free detergent. Samples of 100 grams each of this detergent are admixed with 0.10, 0.15, 0.20 and 0.25 grams of each of the substances as set forth in Table II of Example VII. Each of the detergent samples has an excellent aroma as indicated in Table II of Example VII.

EXAMPLE XII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table II of Example VII.

Fabric softening compositions prepared according to Example I at column 15 of U.S. Pat. No. 3,632,396 having aroma characteristics as set forth in Table II of Example VII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener nonwoven fabrics and these aroma characteristics are described in Table II of Example VII, supra.

EXAMPLE XIII

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the copolymer is dissolved in the alcohol. The following ingredients are added to the PVP/VA alcoholic solution:

| INGREDIENT | WEIGHT PERCENT |
|---|---|
| Dioctyl sebacate | 0.05% |
| Benzyl alcohol | 0.10% |
| Dow Corning 473 fluid (prepared by the Dow Corning Corporation) | 0.10% |
| Tween 20 surfactant (prepared by ICI America Corporation) | 0.03% |
| One of the perfumery substances as set forth in Table II of Example VII | 0.10% |

The perfuming substances as set forth in Table II of Example VII add aroma characteristics as set forth in Table II of Example VII after which are rather intense and aesthetically pleasing to the users of the soft-feel, good-hold pump hair sprays.

EXAMPLE XIV

CONDITIONING SHAMPOOS

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example VII is added to the mixture. The resulting mixture is cooled to 40° C. and blending is carried out for an additional one hour in each case. At the end of this blending period, the resulting material has a pleasant fragrance as indicated in Table II of Example VII.

EXAMPLE XV

Scented polyethylene pellets having a pronounced scent as set forth in Table II of Example VII are prepared as follows:

75 Pounds of polyethylene of a melting point of about 200° F. are heated to about 230° F. in a container of the kind illustrated in FIGS. 11 and 12. 25 Pounds of each of the perfume materials of Table II of Example VII, supra, are then added quickly to the liquified polyethylene. The lid 228 is put in place and the agitating means 273 are actuated. The temperature is maintained at about 225° F. and the mixing is then continued for about 5-15 minutes. The valve "V" is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table II of Example VII, supra, are then formed. Analysis demonstrates that the pellets contain about 25% of each of the perfume substances of Table II of Example VII so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets of films. The sheets or films have a pronounced aroma as set forth in Table II of Example VII, supra. The sheets are also fabricated into garbage bags which have aromas as set forth in Table II of Example VII, supra.

What is claimed is:

1. A mixture of chemicals having a pronounced leathery aroma consisting essentially of:

"A": At least one substance having the structure:

$$R_9 \overset{X}{\diagup} R_{10}$$

$$\left(\begin{array}{c} O \\ \| \\ -C- \end{array}\right) \text{ and } \left(\begin{array}{c} OH \\ | \\ -C- \\ | \\ H \end{array}\right);$$

"B": At least one compound having the structure:

[benzene ring with substituents $R_{12}$, $R_{13}$, $R_{14}$, $R_{15}$]

in an amount of from about 3 up to about 7% wherein each of $R_{12}$–$R_{15}$ represents hydrogen or $C_1$–$C_4$ alkyl with the proviso that at least two of $R_{12}$–$R_{15}$ represents hydrogen;

"C": At least one compound having the structure:

[benzene ring with OH and substituents $R_1$, $R_2$, $R_3$, $R_4$, $R_5$]

in an amount of from about 2% up to about 6% wherein $R_1$, $R_2$, $R_3$, $R_4$ and $R_5$ each represents hydrogen or $C_1$–$C_4$ alkyl with the proviso that one, two or three of $R_1$, $R_2$, $R_3$, $R_4$ and $R_5$ represents $C_1$–$C_4$ alkyl;

"D": Optionally, at least one compound having the structure:

[naphthalene with $R_{11}$ and $R_6$]

in an amount of from 0% up to about 1.2% wherein $R_6$ represents hydrogen or methyl and $R_{11}$ represents hydrogen or methyl with the proviso that at least one of $R_6$ or $R_{11}$ is hydrogen;

"E": At least one compound defined according to the structure:

$$R_7-\overset{\overset{O}{\|}}{C}-O-R_8$$

in an amount of from about 30% up to about 70% wherein $R_7$ represents $C_{11}$, $C_{13}$, or $C_{15}$ straight-chain alkyl and $R_8$ represents $C_1$–$C_3$ lower alkyl;

"F": At least one compound having the structure:

$$H_3C \overset{(CH_2)_n}{\diagup} CH_3$$

in an amount of from about 20% up to about 60% wherein n represents an integer of from 8 up to 28;

"G": Optionally, the compound having the structure:

[structure of isopropyl malonate diester]

in an amount of from 0 up to about 6%; and

"H": Optionally, the compound having the structure:

[p-isobutylphenyl acetate structure]

in an amount of from 0 up to about 6% with the requirement that:

$$\Sigma[A + B + C + D + E + F + G + H]$$

equal 100%.

2. A process for augmenting or enhancing the aroma of a consumable material selected from the group consisting of perfume compositions, perfumed polymers, colognes and perfumed articles comprising the step of adding to said consumable material an aroma augmenting or enhancing quantity of the composition of matter defined according to claim 1.

3. The process of claim 2 wherein the consumable material is a perfume composition.

4. The process of claim 2 wherein the consumable material is a cologne.

5. The process of claim 2 wherein the consumable material is a perfumed article.

6. The process of claim 2 wherein the consumable material is a perfumed article and the perfumed article is a solid or liquid anionic, cationic, nonionic or zwitterionic detergent.

7. The process of claim 2 wherein the consumable material is a perfumed article and the perfumed article is a fabric softener composition or fabric softener article.

8. The process of claim 2 wherein the consumable material is a perfumed article and the perfumed article is a hair preparation.

9. The process of claim 2 wherein the consumable material is a perfumed polymer and the perfumed polymer is a synthetic leather polymer.

* * * * *

UNITED STATES PATENT AND TRADEMARK OFFICE
CERTIFICATE OF CORRECTION

PATENT NO. : 4,595,525
DATED : June 17, 1986
INVENTOR(S) : Braja D. Mookherjee, et al It is certified that error appears in the above-identified patent and that said Letters Patent are hereby corrected as shown below:

Column 6, line 48, replace "polmatate" with:

---palmitate---.

Column 32, line 62, replace "nonadecane" with:

--- n-nonadecane---.

Column 35, line 43, replace "Isopentone" with:

---Isopentane---.

Column 45, line 21, after the structure:

add:

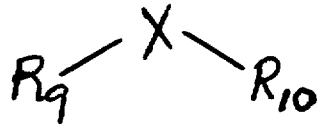

---in an amount of from about 1% up to about 5% wherein $R_9$ represents $C_9$-$C_{11}$ straight-chain alkyl and wherein $R_{10}$ represents methyl and X is a moiety selected from the group consisting of:---.

Signed and Sealed this

Fourth Day of November, 1986

[SEAL]

Attest:

DONALD J. QUIGG

Attesting Officer     Commissioner of Patents and Trademarks